United States Patent
Wang et al.

(10) Patent No.: US 11,162,935 B2
(45) Date of Patent: Nov. 2, 2021

(54) SYSTEMS AND METHODS FOR SEPARATING, DETECTING, AND QUANTIFYING A TARGET POLYNUCLEOTIDE

(71) Applicant: University of Notre Dame du Lac, Notre Dame, IN (US)

(72) Inventors: Ceming Wang, South Bend, IN (US); Satyajyoti Senapati, South Bend, IN (US); Hsueh-Chia Chang, South Bend, IN (US)

(73) Assignee: University of Notre Dame du Lac, Notre Dame, IN (US)

(*) Notice: Subject to any disclaimer, the term of this patent is extended or adjusted under 35 U.S.C. 154(b) by 149 days.

(21) Appl. No.: 16/550,766

(22) Filed: Aug. 26, 2019

(65) Prior Publication Data

US 2020/0064328 A1    Feb. 27, 2020

Related U.S. Application Data

(60) Provisional application No. 62/722,692, filed on Aug. 24, 2018.

(51) Int. Cl.
*C12Q 1/68* (2018.01)
*G01N 33/487* (2006.01)

(52) U.S. Cl.
CPC ......... *G01N 33/48721* (2013.01); *C12Q 1/68* (2013.01)

(58) Field of Classification Search
CPC ...................................................... C12G 1/68

USPC ............................................................ 435/6
See application file for complete search history.

(56) References Cited

U.S. PATENT DOCUMENTS

| | | | |
|---|---|---|---|
| 4,369,370 A | 1/1983 | Spohr | |
| 6,428,959 B1 | 8/2002 | Deamer | |
| 6,617,113 B2 | 9/2003 | Deamer | |
| 8,206,568 B2 | 6/2012 | Branton et al. | |
| 2011/0139707 A1* | 6/2011 | Siwy | B01D 67/0062 210/500.21 |
| 2013/0092541 A1 | 4/2013 | Drndic et al. | |
| 2015/0148436 A1* | 5/2015 | Small | B01D 67/0034 521/53 |
| 2018/0080072 A1 | 3/2018 | Li et al. | |

FOREIGN PATENT DOCUMENTS

WO  WO 2012/009578 A2   1/2012

OTHER PUBLICATIONS

Ceming et al, Atomic layer deposition modified track-etched conical nanochannels for protein sensing, Anal Chem. Aug. 18, 2015;87(16):8227-33. doi: 10.1021/acs.analchem.5b01501. Epub Aug. 3, 2015.*

(Continued)

*Primary Examiner* — Aaron A Priest
(74) *Attorney, Agent, or Firm* — Michael Best & Friedrich LLP

(57) ABSTRACT

Systems and methods for controlling molecular translocation in solid-state nanopores by edge field leakage. The system dramatically reduces (by orders of magnitude) and controls the fast electrophoretic velocity of molecules to realize sensitive and selective solid-state nanopore sensors for polynucleotides and sequencing platforms.

21 Claims, 35 Drawing Sheets

(56) References Cited

OTHER PUBLICATIONS

Apel et al, Shedding light on the mechanism of asymmetric track etching: an interplay between latent track structure, etchant diffusion and osmotic flow, Phys Chem Chem Phys. Sep. 14, 2016;18(36):25421-25433. doi: 10.1039/c6cp05465j.*

Apel et al., "Accurate characterization of single track-etched, conical nanopores ," Physical Chemistry Chemical Physics, Jun. 2014, 16:15214-15223.

Apel et al., "Diode-like single-ion track membrane prepared by electro-stopping," Nuclear Instruments and Methods in Physics Research Section B: Beam Interactions with Materials and Atoms, Nov. 2001, 184(3):337-346.

Apel et al., "Shedding light on the mechanism of asymmetric track etching: an interplay between latent track structure, etchant diffusion and osmotic flow," Physical Chemistry Chemical Physics, Sep. 2016, 18:25421-25433.

Banerjee et al., "Nanotubular metal—insulator—metal capacitor arrays for energy storage," Nature Nanotechnology, May 2009, 4(5):292-296.

Banerjee et al., "Slowing DNA Transport Using Graphene—DNA Interactions," Advanced Functional Materials, Feb. 2015, 25(6):936-946.

Branton et al., "The potential and challenges of nanopore sequencing," Nature Biotechnology, Oct. 2008, 26(10):1146-1153.

Cameron et al., "Atomic layer deposition of $SiO_2$ and $TiO_2$ in alumina tubular membranes: pore reduction and effect of surface species on gas transport," Langmuir, Jun. 2000, 16(19):7435-7444.

Chen et al., "Atomic layer deposition to fine-tune the surface properties and diameters of fabricated nanopores," Nano Letters, Jun. 2004, 4(7):1333-1337.

Chen et al., "Characterization of microRNAs in serum: a novel class of biomarkers for diagnosis of cancer and other diseases," Cell Res, Oct. 2008, 18(10):997-1006.

Chen et al., "DNA translocation through an array of kinked nanopores," Nature Materials, Aug. 2010, 9(8):667-675.

Cheng et al., "Nanofluidic diodes," Chemical Society Reviews, Mar. 2010, 39(3):923-938.

Deamer et al., "Three decades of nanopore sequencing,"Nature Biotechnology, May 2016, 34(5):518-524.

Dekker, "Solid-state nanopores," Nature Nanotechnology, Apr. 2007, 2(4):209-215.

Egatz-Gomez et al., "Future microfluidic and nanofluidic modular platforms for nucleic acid liquid biopsy in precision medicine," Biomicrofluidics, May 2016, 10(3):032902, 27 pages.

Elam et al., "Atomic layer deposition for the conformal coating of nanoporous materials," Journal of Nanomaterials, Jul. 2006, 64501 (5 pages).

Elam et al., "Conformal coating on ultrahigh-aspect-ratio nanopores of anodic alumina by atomic layer deposition," Chemistry of Materials, Sep. 2003, 15(18):3507-3517.

Fischer et al., "Production and use of nuclear tracks: imprinting structure on solids," Reviews of Modern Physics, Oct. 1983, 55(4):907-948.

George, "Atomic layer deposition: an overview," Chemical Reviews, Jan. 2010, 110(1):111-131.

Gordon et al., "A kinetic model for step coverage by atomic layer deposition in narrow holes or trenches," Chemical Vapor Deposition, Mar. 2003, 9(2):73-78.

Grigoras et al., "Coating of nanoporous membranes: atomic layer deposition versus sputtering," Journal of Nanoscience and Nanotechnology, Jun. 2009, 9(6):3763-3770.

Hafner et al., "RNA-ligase-dependent biases in miRNA representation in deep-sequenced small RNA cDNA libraries," RNA, Jul. 2011, 17(9):1697-1712.

Karnik et al., "Electrostatic control of ions and molecules in nanofluidic transistors," Nano Letters, Mar. 2005, 5(5):943-948.

Kasianowicz et al., "Characterization of individual polynucleotide molecules using a membrane channel," Proceedings of the National Academy of Sciences of the United States of America, Nov. 1996, 93(24):13770-13773.

Kawano et al., "Controlling the Translocation of Single-Stranded DNA through α-Hemolysin Ion Channels Using Viscosity," Langmuir, Jan. 2009, 25(2):1233-1237.

Knez et al., "Synthesis and surface engineering of complex nanostructures by atomic layer deposition," Advanced Materials, Nov. 2007, 19(21):3425-3438.

Krapf et al., "Fabrication and characterization of nanopore-based electrodes with radii down to 2nm," Nano Letters, Jan. 2006, 6(1):105-109.

Larkin et al., "Slow DNA Transport through Nanopores in Hafnium Oxide Membranes," ACS Nano, Oct. 2013, 7(11):10121-10128.

Li et al., "Ion-beam sculpting at nanometre length scales," Nature, Jul. 2001, 412(6843):166-169.

Li et al., "Precise pore size tuning and surface modifications of polymeric membranes using the atomic layer deposition technique," Journal of Membrane Science, Dec. 2011, 385-386:1-9.

Manrao et al., "Reading DNA at single-nucleotide resolution with a mutant MspA nanopore and phi29 DNA polymerase," Nature Biotechnology, Apr. 2012, 30:349-353.

Martin, "Nanomaterials: a membrane-based synthetic approach," Science, Dec. 1994, 266(5193):1961-1966.

Masuda et al., "Highly ordered nanochannel-array architecture in anodic alumina," Applied Physics Letters, Nov. 1997, 71(19):2770-2772.

Meller et al., "Single Molecule Measurements of DNA Transport through a Nanopore," Electrophoresis, Aug. 2002, 23(16):2583-2591.

Meller et al., "Voltage-Driven DNA Translocations through a Nanopore," Physical Review Letters, Apr. 2001, 86:3435-3438.

Nam et al., "Ionic field effect transistors with sub-10 nm multiple nanopores," Nano Letters, Apr. 2009, 9(5):2044-2048.

Nam et al., "Sub-10-nm nanochannels by self-sealing and self-limiting atomic layer deposition," Nano Letters, Aug. 2010, 10(9):3324-3329.

Pardon et al., "Pt—Al2O3 dual layer atomic layer deposition coating in high aspect ratio nanopores," Nanotechnology, Jan. 2013, 24(1):015602, 11 pages.

Pritchard et al., "MicroRNA profiling: approaches and considerations," Nature Review: Genetics, May 2012, 13(5):358-369.

Puurunen, "Surface chemistry of atomic layer deposition: A case study for the trimethylaluminum/water process," Journal of Applied Physics, Jun. 2005, 97(12): 121301 (52 pages).

Rhee et al., "Nanopore sequencing technology: research trends and applications," Trends in Biotechnology, Dec. 2006, 24(12): 580-586.

Sander et al., "Template-assisted fabrication of dense, aligned arrays of titania nanotubes with well-controlled dimensions on substrates," Advanced Materials, Nov. 2004, 16(22):2052-2057.

Santarius et al., "A census of amplified and overexpressed human cancer genes," Nature Reviews: Cancer, Jan. 2010, 10:59-64.

Schoch et al., Transport phenomena in nanofluidics, Reviews of Modern Physics, Jul. 2008, 80(3):839-883.

Shin et al., "Formation of $TiO_2$ and $ZrO_2$ nanotubes using atomic layer deposition with ultraprecise control of the wall thickness," Advanced Materials, Jul. 2004, 16(14):1197-1200.

Skinner et al., "Distinguishing Single- and Double-stranded Nucleic Acid Molecules using Solid-State Nanopores," Nano Letters, Aug. 2009, 9(8):2953-2960.

Smeets et al., "Noise in solid-state nanopores," Proceedings of the National Academy of Sciences of the United States of America, Jan. 2008, 105(2):417-421.

Stein et al., "Ion-beam sculpting time scales," Physical Review Letters, Dec. 2002, 89(27):276106 (4 pages).

Storm et al., "Electron-beam-induced deformations of $SiO_2$ nanostructures," Journal of Applied Physics, Jul. 2005, 98(1):014307 (8 pages).

(56) References Cited

OTHER PUBLICATIONS

Storm et al., "Fabrication of solid-state nanopores with single-nanometre precision," Nature Materials, Aug. 2003, 2(8):537-540.

Stroeve et al., "Biotechnical and other applications of nanoporous membranes," Trends in Biotechnology, Jun. 2011, 29(6):259-266.

Tan et al., "Combining atomic layer deposition with a template-assisted approach to fabricate size-reduced nanowire arrays on substrates and their electrochemical characterization," Journal of Physical Chemistry C, Mar. 2007, 111(13):4964-4968.

Thamida et al., "Nonlinear electrokinetic ejection and entrainment due to polarization at nearlt insulated wedges," Physics of Fluids, Dec. 2002, 14(12):4315-4328.

VanDersarl et al., "Nanostraws for direct fluidic intracellular access," Nano Letters, Aug. 2012, 12(8):3881-3886.

Venkatesan et al., "DNA sensing using nano-crystalline surface-enhanced $Al_2O_3$ nanopore sensors," Advanced Functional Materials, Apr. 2010, 20(8):1266-1275.

Venkatesan et al., "Highly sensitive, mechanically stable nanopore sensors for DNA analysis," Advanced Materials, Jul. 2009, 21(27):2771-2776.

Venkatesan et al., "Nanopore sensors for nucleic acid analysis," Nature Nanotechnology, Oct. 2011, 6(10):615-624.

Wang et al., "Atomic Layer Deposition Modified Track-Etched Conical Nanochannels for Protein Sensing," Analytical Chemistry, Jul. 2015, 87(16):8227-8233.

Wang et al., "Low-voltage electroosmotic pumps fabricated from track-etched polymer membranes," Lab on a Chip, May 2012, 12(9):1710-1716.

Wang et al., "Nanopore-based detection of circulating microRNAs in lung cancer patients," Nature Nanotechnology, Oct. 2011, 6:668-674.

Wanunu et al., "DNA Translocation Governed by Interactions with Solid-State Nanopores," Biophysical Journal, Nov. 2008, 95(10):4716-4725.

Wanunu et al., "Rapid electronic detection of probe-specific microRNAs using thin nanopore sensors," Nature Nanotechnology, Nov. 2010, 5:807-814.

Wanunu, "Nanopores: A journey towards DNA sequencing," Physics of Life Reviews, May 2012, 9(2):125-158.

Yan et al., "Ion current rectification inversion in conic nanopores: Nonequilibrium ion transport biased by ion selectivity and spatial asymetry," The Journal of Chemical Physics, Jan. 2013, 138:044706, 6 pages.

Yang et al., "Low-temperature growth of ZnO nanorods in anodic aluminum oxide on Si substrate by atomic layer deposition," Applied Physics Letters, Jan. 2007, 90(3):033104 (3 pages).

\* cited by examiner

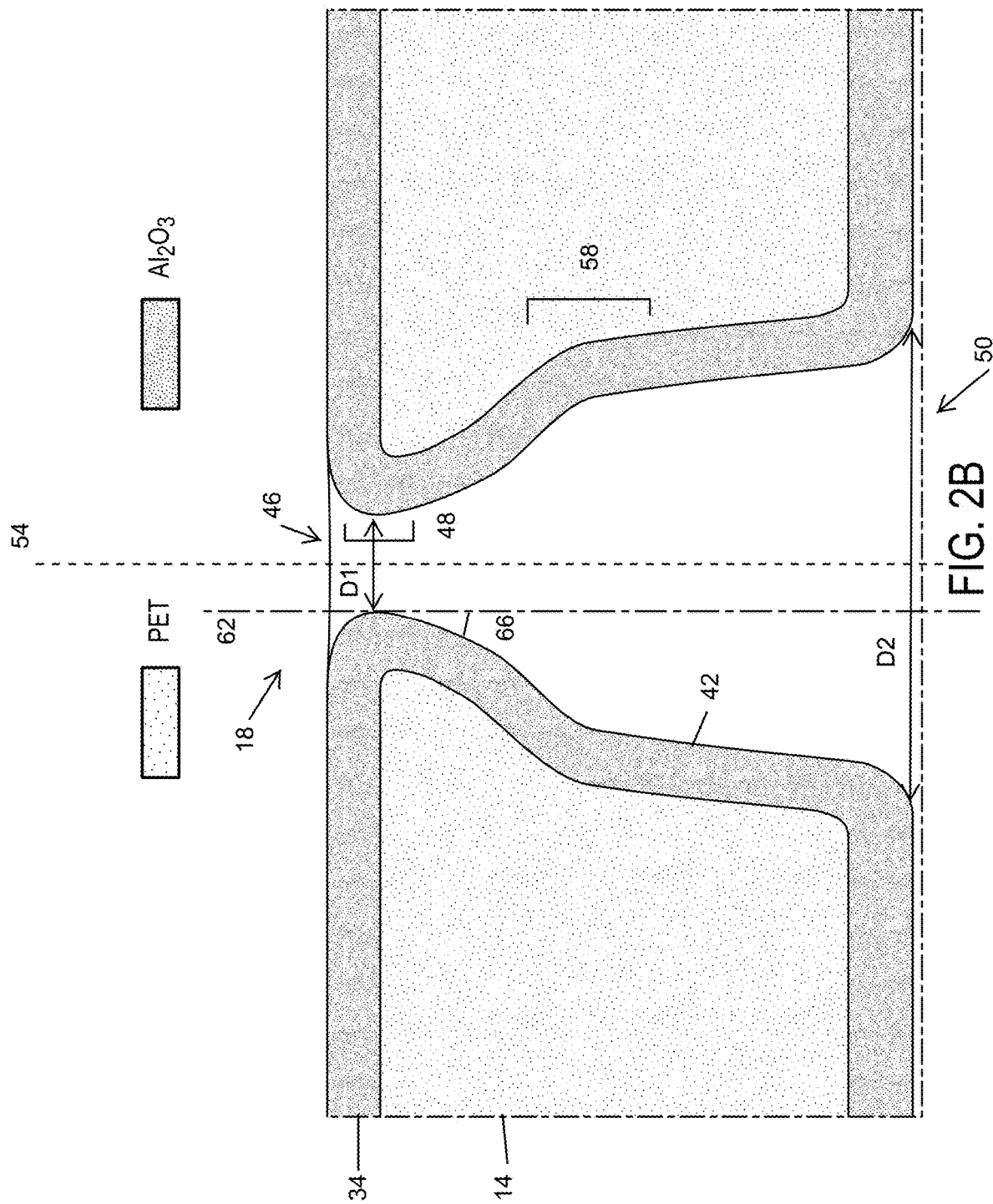

SYSTEMS AND METHODS FOR SEPARATING, DETECTING, AND QUANTIFYING A TARGET POLYNUCLEOTIDE

CROSS-REFERENCE TO RELATED APPLICATION(S)

This application is a non-provisional of and claims priority to U.S. Provisional Patent Application No. 62/722,692, filed on Aug. 24, 2018, the entire contents of which are fully incorporated herein by reference.

TECHNICAL FIELD

The present disclosure relates to systems and methods for separating, and quantifying single stranded polynucleotides such as polynucleotides or polypeptides by controlling translocation dynamics.

BACKGROUND OF THE INVENTION

Solid-state nanopore based technologies are emerging as next generation bio-nanosensors for the electrical detection, analysis, and manipulation of single stranded polynucleotides, applicable to polynucleotide sequencing. Nanopore-based sensing is attractive for studying individual polynucleotides because it is a label-free, amplification free, single-molecule approach that can potentially be scaled up for high-throughput polynucleotide analysis. A major technological bottleneck is a reliable method for controlling the single stranded polynucleotides translocation time to enhance sensing resolution.

Enzyme-less voltage driven translocation of polynucleotides through solid-state nanopores offers higher throughput. However, it suffers from an excessively short translocation time to identify any feature of the translocating polynucleotides from the amplitude and duration of the resistive signal. Simple techniques for reducing the velocity of translocating single stranded polynucleotides, such as lowering the experimental temperature or increasing the viscosity of the solution, also reduce the current signal and therefore do not improve signal-to-noise ratio.

The use of single stranded polynucleotide-pore interaction is a promising option for regulating polynucleotide transport without degrading the signal-to-noise ratio. However, significant delay of single stranded polynucleotide translocation via nanopore interaction is not present due to a lack of understanding of the underlying mechanism. A new strategy to control the voltage-driven transport of single stranded polynucleotide to induce strong electrostatic single stranded polynucleotide-pore interaction can be used to optimize the translocation time and throughput of any assay.

BRIEF SUMMARY OF THE INVENTION

In a first aspect, the invention provides a system for detecting and quantifying a target single stranded polynucleotide. The system comprising: a membrane including a plurality of nanopores extending between a lower surface and an upper surface of the membrane. Each of the nanopores include a first opening and a second opening thereby defining a passageway through the membrane, a dielectric material coating the passageway and at least a portion of the upper surface. The passageway defines a first longitudinal axis and includes a first inner diameter at the first opening and a second inner diameter at the second opening, and the first diameter is smaller than the second diameter. The passageway diverges from the first opening to a first section of the passageway at a first slope and the passageway diverges from the first section to the second opening at a second slope. The first opening intersects the upper surface at the first inner diameter, and a second longitudinal axis, parallel to the longitudinal axis, intersects the first inner diameter and defines an angle with an adjacent inner surface of the passageway. The application of an electric field to the membrane traps the single stranded polynucleotide at the first opening.

In a further aspect, the invention provides a method of delaying translocation of a target single stranded polynucleotide, comprising applying an electric field to a membrane having a nanopore edge to enhance a leakage field. The membrane includes a plurality of nanopores extending between a lower surface and an upper surface of the membrane. Each of the nanopores include a first opening and a second opening thereby defining a passageway through the membrane with a dielectric material coating the passageway and at least a portion of the upper surface. The passageway defines a first longitudinal axis and includes a first inner diameter at the first opening and a second inner diameter at the second opening. The first inner diameter is smaller than the second inner diameter. The passageway diverges from the first opening to a first section of the passageway at a first slope and the passageway diverges from the first section to the second opening at a second slope. The first opening intersects the upper surface at the first inner diameter, and a second longitudinal axis, parallel to the first longitudinal axis, intersects the first inner diameter and defines an angle with an adjacent inner surface of the passageway, temporarily trapping the target single stranded polynucleotide at the first opening.

BRIEF DESCRIPTIONS OF THE DRAWINGS

FIG. 2B is an enlarged portion of the system illustrated in FIG. 1.

Figure 4:
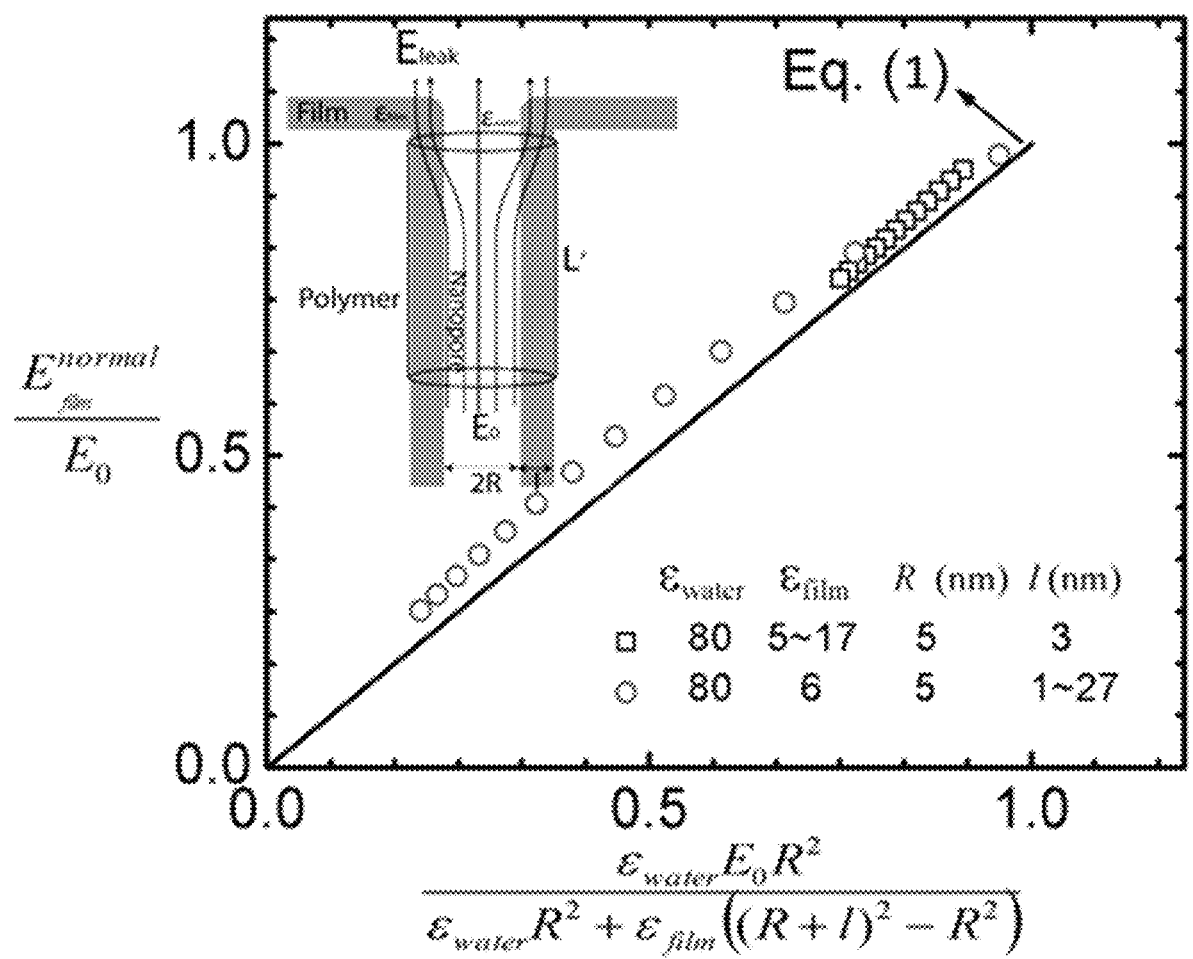

FIG. 4 graphically illustrates the collapse of numerical data for normal field leakage in the dielectric film for different film permittivities and film thicknesses. Inset shows the schematics of a high-permittivity dielectric film on an insulating polymer nanopore orifice and the Gauss volume used to estimate the leaked field around the pore.

Figures 5A, 5B:
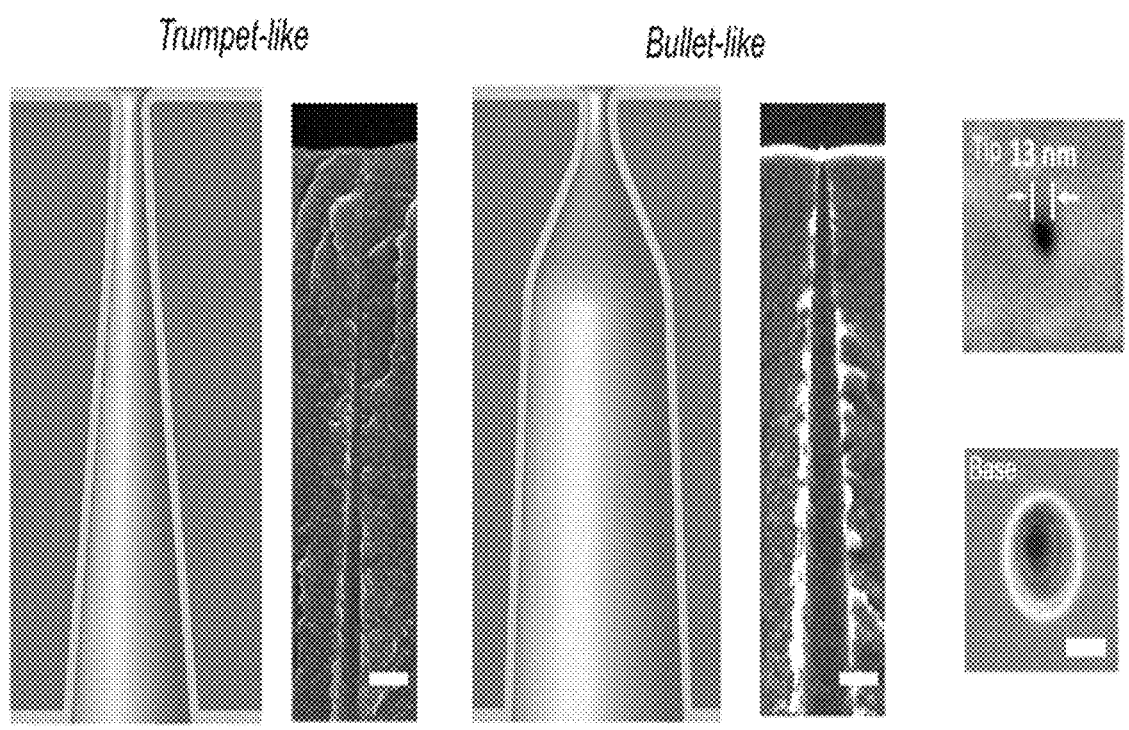

FIG. 5A is a schematic illustration (not to scale) and cross-sectional SEM images of a trumpet-like nanopore (left) after etching breakthrough and a bullet-like nanopore (right) after extended etching. Scale bar=400 nm.

FIG. 5B are representative SEM images of the tip side (top) and the base side (bottom) of an ALD $Al_2O_3$ coated polymeric nanopore. Scale bar=500 nm.

Figure 6:
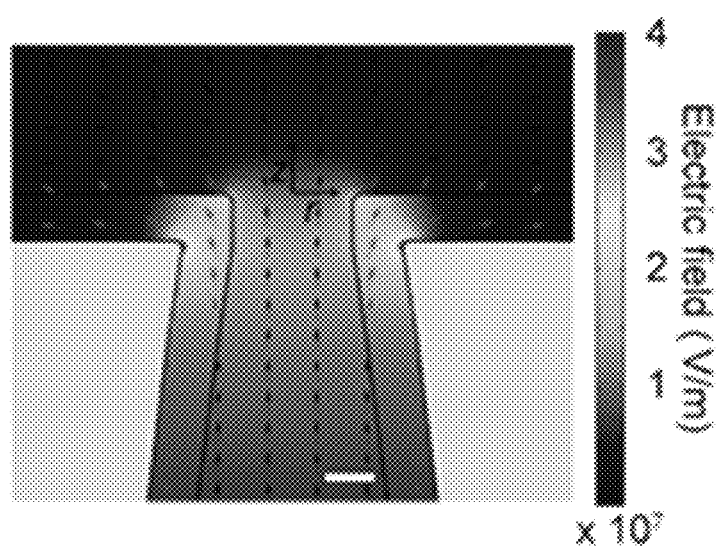
Figure 7:
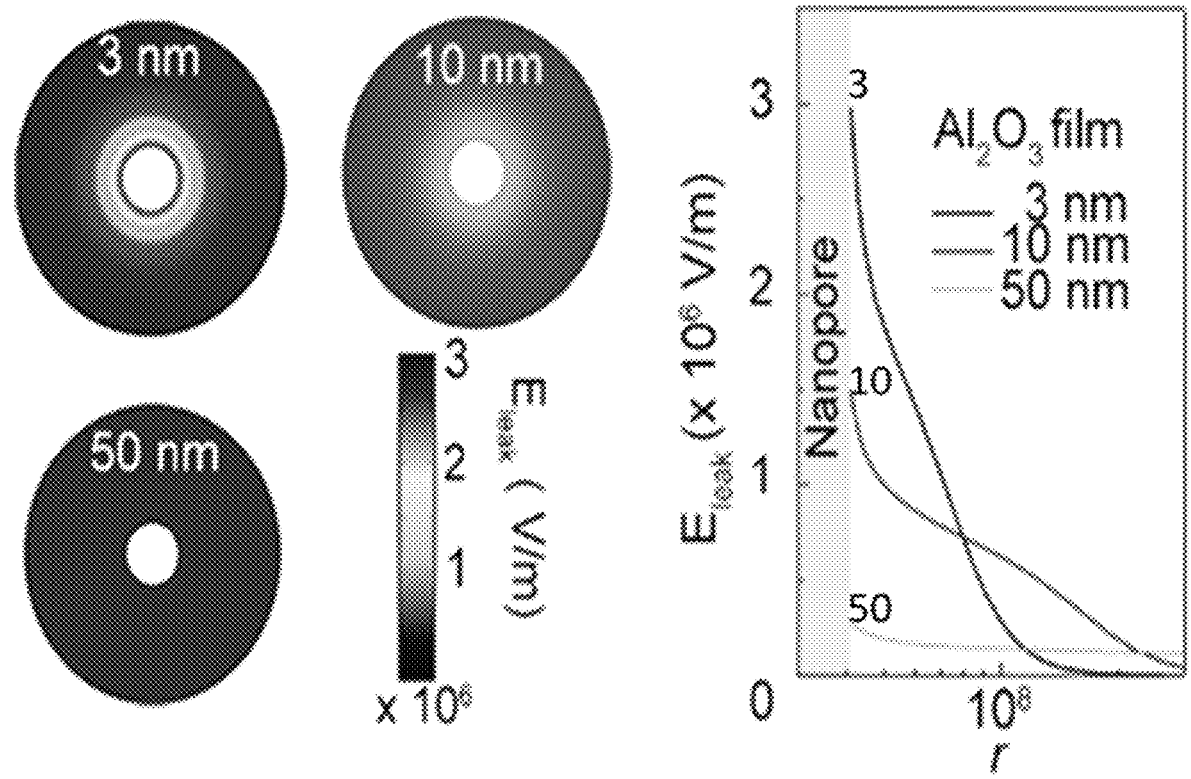

FIG. 6 is a two-dimensional-axisymmetric electrostatic modelling of a $Al_2O_3$-coated bullet-like nanopore (tip diameter: 8 nm, half cone angle: 8°) was simulated with an applied voltage of 0.5 V. Electric field lines and intensity evaluated numerically on the tip side of the $Al_2O_3$-coated polymer nanopore. The electric field is significantly enhanced and develops a normal field leakage near the sharp pore edge. Scale bar=3 nm FIG. 7 illustrates surface plots of the strength of normal leakage field ($E_{leak}$) showing the normal leakage field at the pore edge is a strong function of $Al_2O_3$ film thickness (nanopore diameter, 8 nm) (left); axial dependence of the normal leakage field as a function of distance from the pore mouth r for three $Al_2O_3$ film thicknesses (right).

Figure 8:
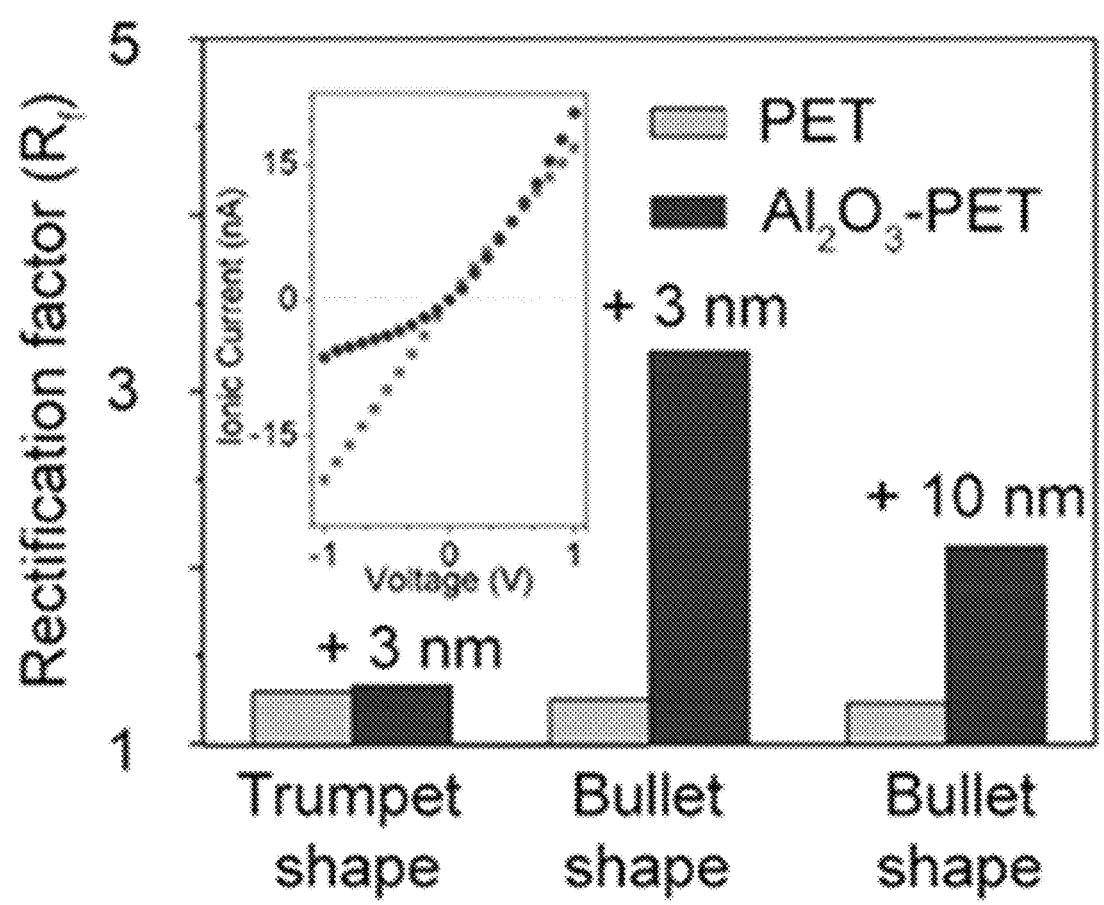

FIG. 8 illustrates the rectification factor for different pores before and after 3 nm or 10 nm $Al_2O_3$ coating (final tip diameter: 10 nm). The bullet-shaped nanopore coated with a thin layer of $Al_2O_3$ film (3 nm) shows the highest degree of rectification, confirming the presence of significant field leakage at the pore tip.

Figure 9:
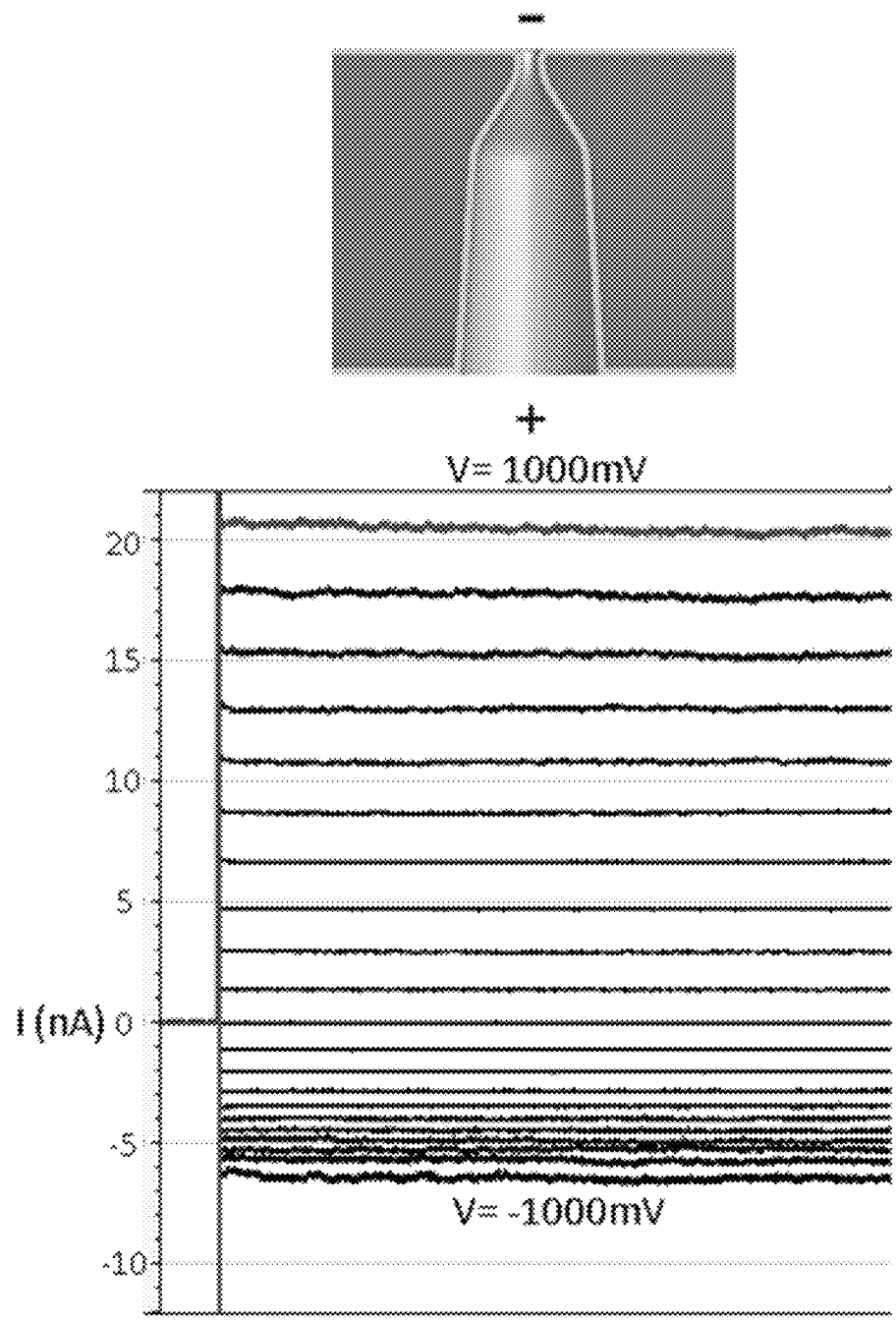

FIG. 9 is a schematic illustration (top) and typical current traces (bottom) of $Al_2O_3$ coated bullet-like polymeric nanopores (10 nm) under applied voltages ranging from −1000 mV to +1000 mV in 1M KCl. These $Al_2O_3$ coated asymmetric polymeric nanopores with bullet-like shape (large cone angles) show strong ionic current rectification behavior, which indicates strong field leakage at the pore tip.

Figure 10:
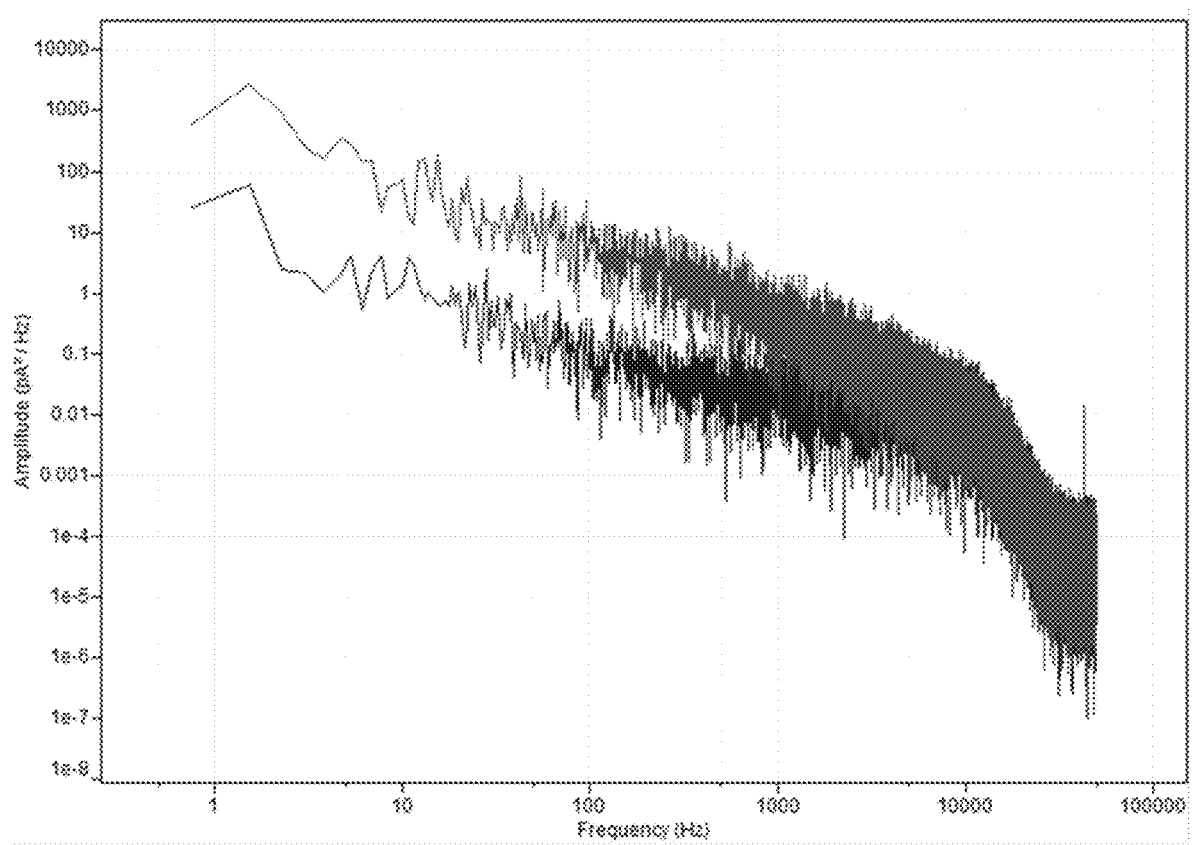

FIG. 10 graphically illustrates current power spectral densities of the bullet-like PET nanopores before (blue) and after (red) 3 nm $Al_2O_3$ coating. The noise characteristics of all $Al_2O_3$-coated PET nanopores showed more than an order of magnitude reduction in higher frequency dielectric noise compared with typical nanopores in dielectric membrane.

Figure 11:
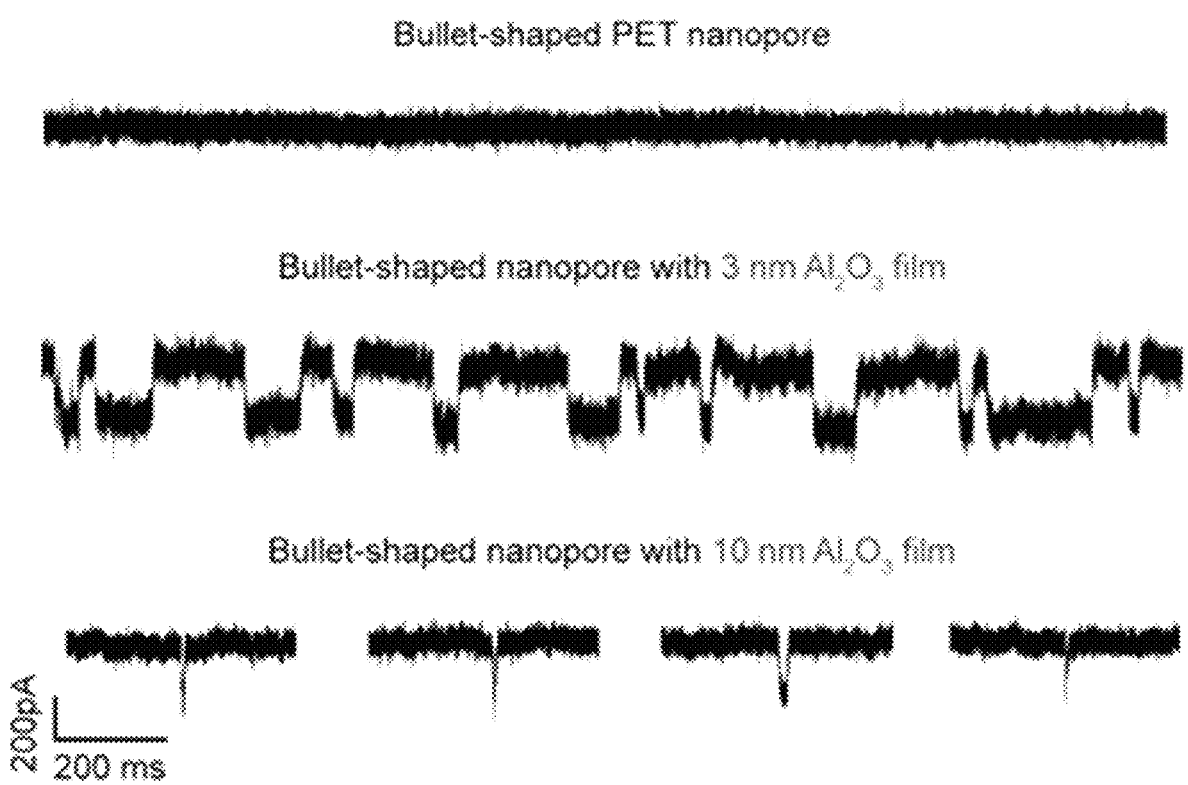

FIG. 11 illustrates representative current traces for 22 nt ssDNA translocation through a bare bullet-shaped PET nanopore without $Al_2O_3$ film coating (diameter, 16 nm) and two bullet-shaped nanopores coated with 3 nm or 10 nm $Al_2O_3$ film under an applied voltage of 500 mV. Both $Al_2O_3$-coated nanopores have the same final tip diameter (10 nm). All three nanopores have similar bullet-like shapes (half cone angle ~7±2°). Slow translocation of 22 nt ssDNA is observed using nanopores with thin $Al_2O_3$ film coating and the average translocation time is a function of film thickness.

Figure 12:
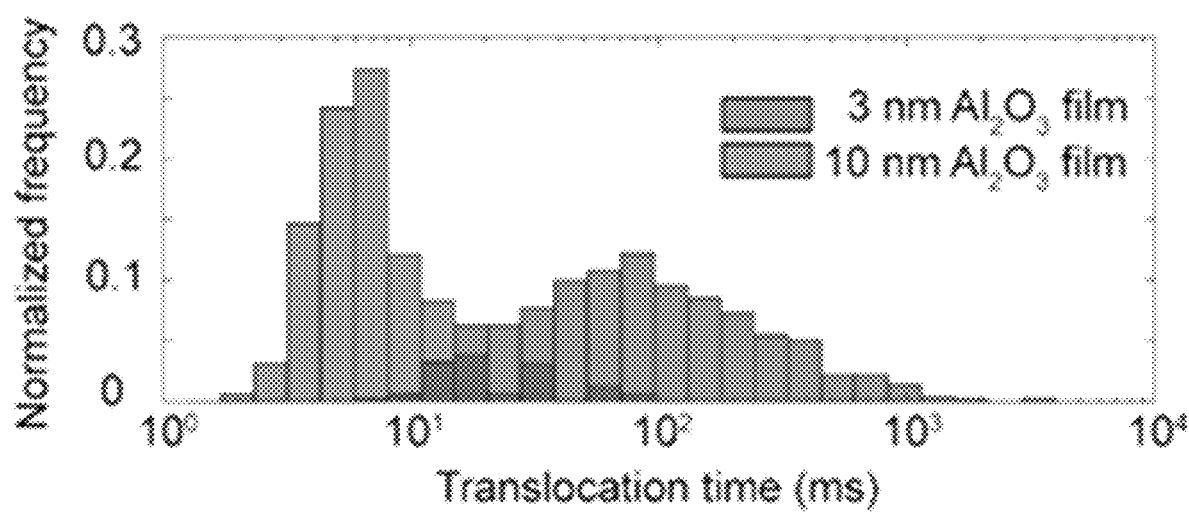

FIG. 12 illustrates normalized histogram of translocation times for nanopores with 3 nm or 10 nm $Al_2O_3$ film. Average translocation time: 3 nm $Al_2O_3$ film, 159 ms; 10 nm, 13 ms.

Figure 13:
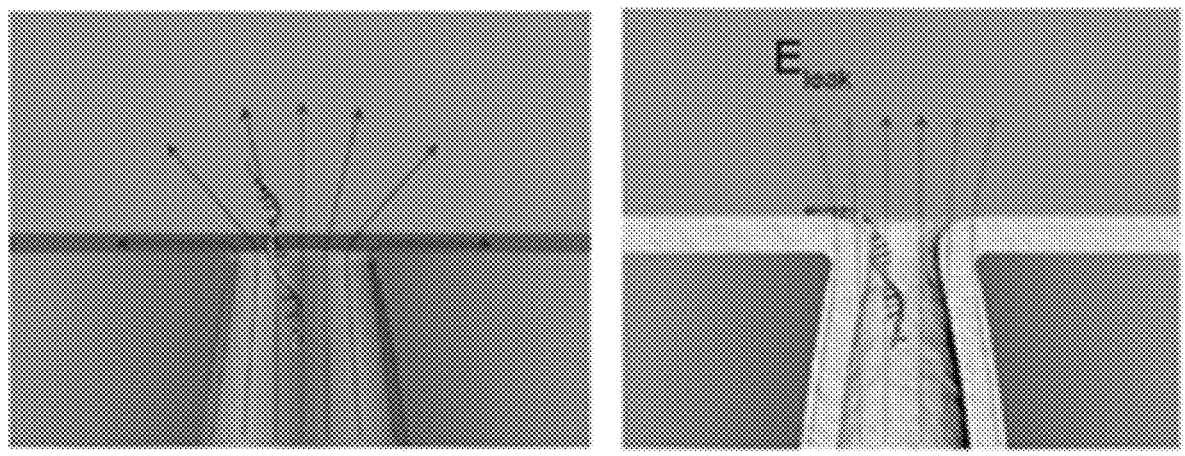

FIG. 13 is a schematic showing the dominant tangential electric field at the bare PET nanopore edge results in a fast translocation of 22 nt ssDNA (left) while the normal leakage field at the $Al_2O_3$-coated nanopore edge traps the ssDNA and thus reduces its mobility (right).

Figure 14:
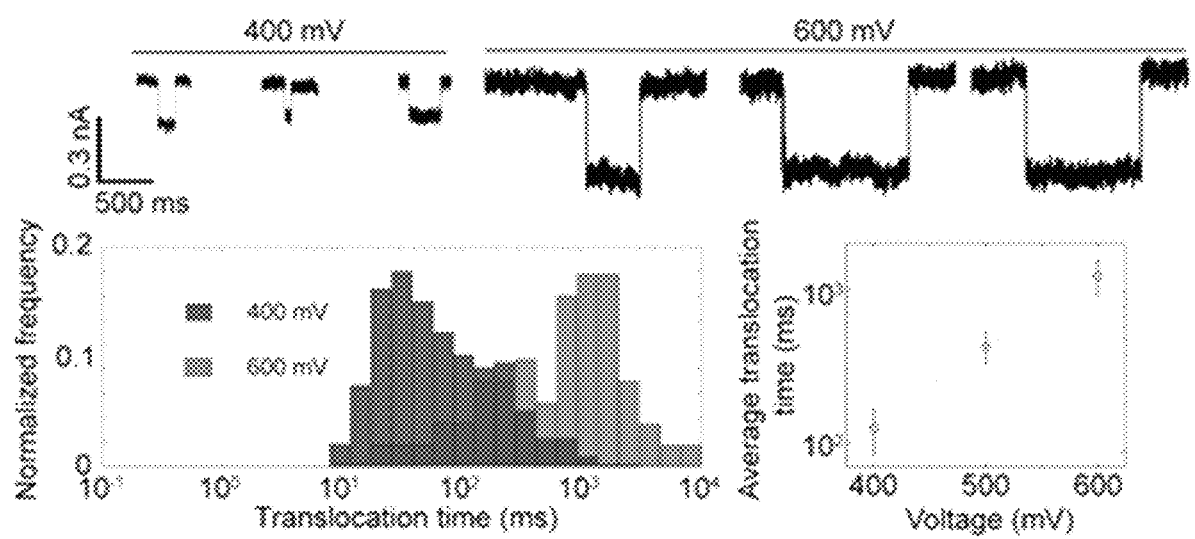

FIG. 14 illustrates representative translocation signals for 22 nt ssDNA translocations at applied voltages of 400 mV and 600 mV (Top); normalized histogram of corresponding translocation times at applied voltages of 400 mV and 600 mV and average translocation time as a function of applied voltage (Bottom).

Figure 15:
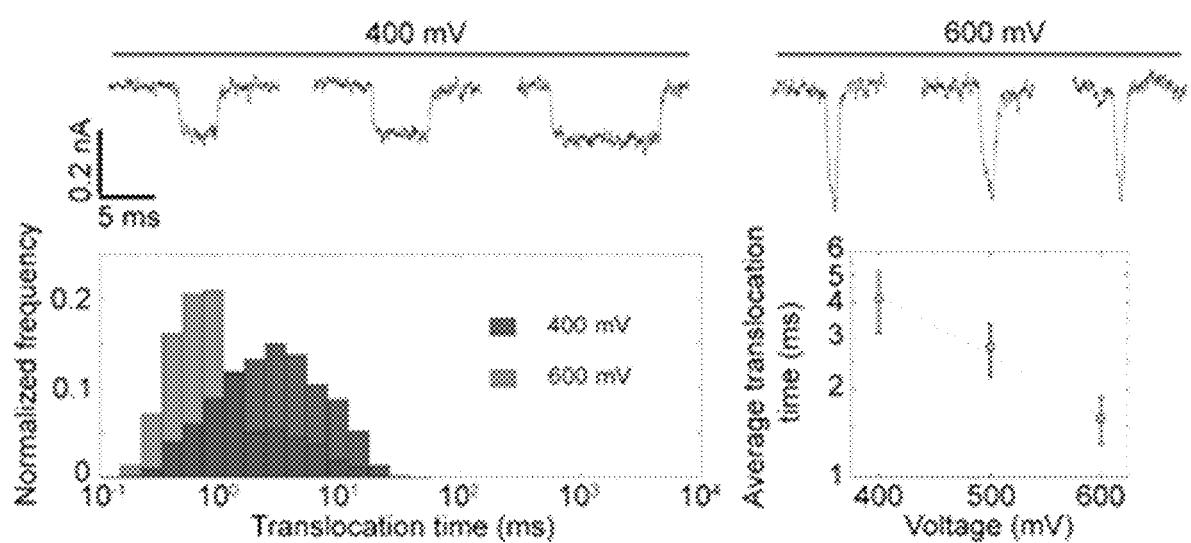

FIG. 15 illustrates representative translocation signals for 22 bp dsDNA translocations at applied voltages of 400 mV and 600 mV (Top); normalized histogram of corresponding translocation times at applied voltages of 400 mV and 600 mV and average translocation time as a function of applied voltage (Bottom). Under the influence of electric field leakage, ssDNA translocates orders of magnitude slower than dsDNA. Data were acquired using the same nanopore coated with 3 nm $Al_2O_3$ film (diameter, 8 nm; half cone angle, 9±2°).

Figure 16:
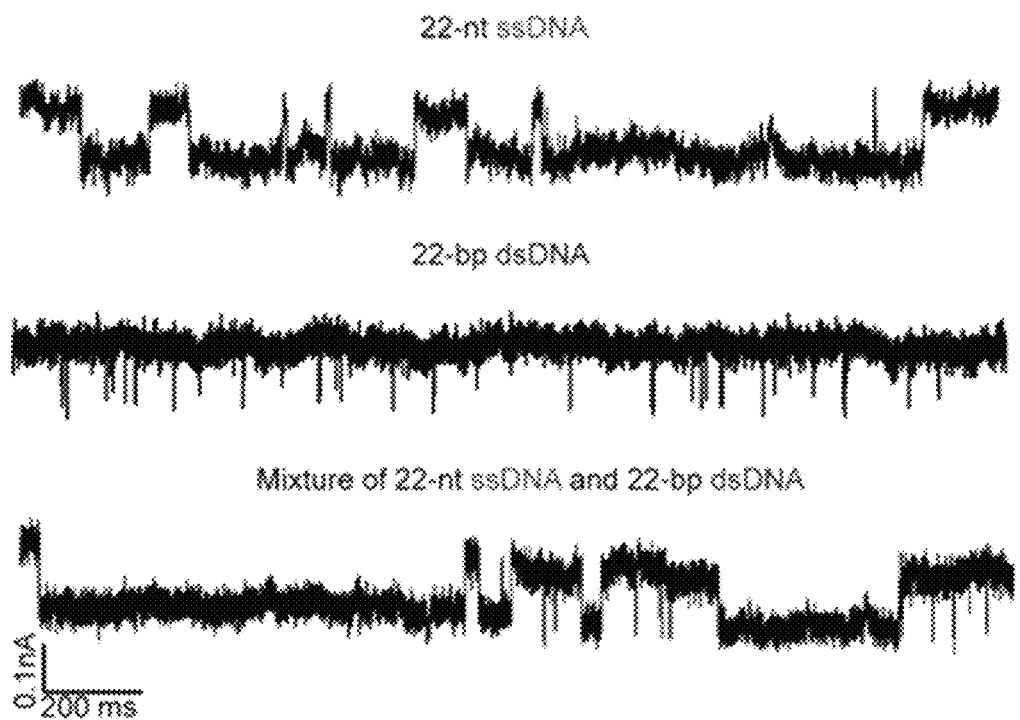

FIG. 16 illustrates representative current traces for 22 nt ssDNA, 22 bp dsDNA, and the mixture of 22 nt ssDNA and 22 bp dsDNA (1:1) translocation through bullet-shaped nanopores (10 nm, half cone angle ~7±2°) coated with 3 nm $Al_2O_3$ film under an applied voltage of 500 mV.

Figure 17:
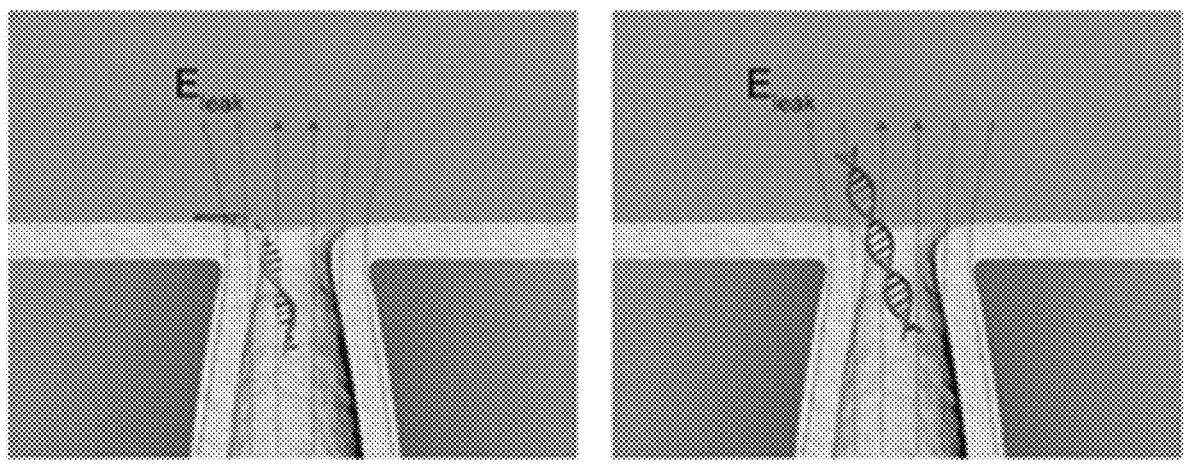

FIG. 17 is a schematic of 22 nt ssDNA (left) and 22 bp dsDNA (right) translocation under the effect of electric field leakage. ssDNA molecules (persistence length, 2 nm) can easily deform and be pinned at the pore edge. The stiffer dsDNA molecule (persistence length, 50 nm) tends to be linearly oriented under the influence of the strong local electric field and could be expected to have weak interactions with the leakage field.

Figure 18:
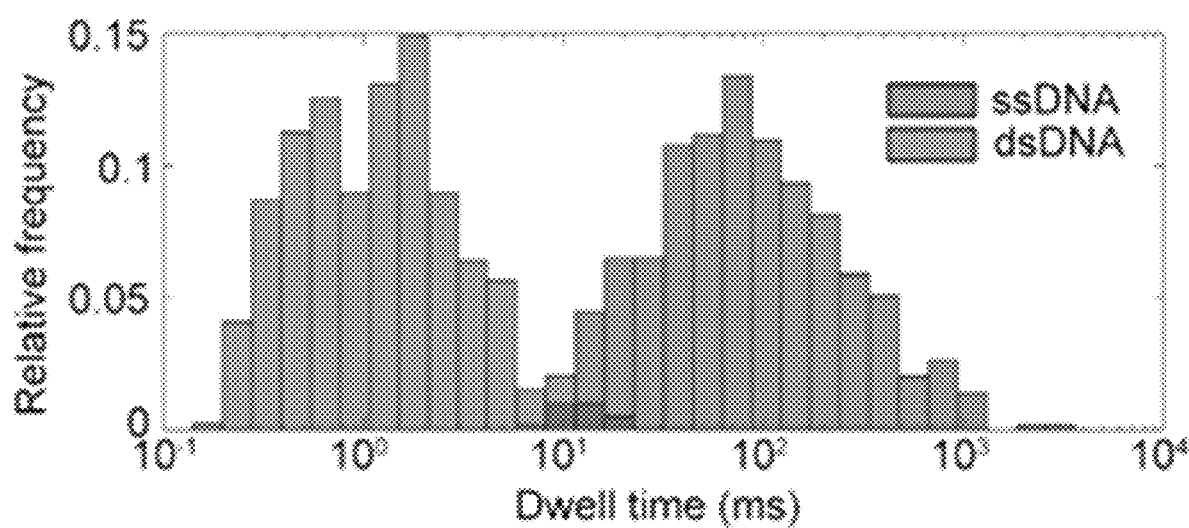

FIG. 18 is a normalized histogram of translocation times for 22 nt ssDNA and 22 bp dsDNA. ssDNA translocates much slower than dsDNA under the effect of electric field leak (for a nanopore with intermediate field leakage, typical translocation time ~1 ms (dsDNA) vs. ~100 ms (ssDNA)). These signature electrical signals allow discrimination (>97%) between ssDNA and dsDNA duplex translocation events.

Figure 19:
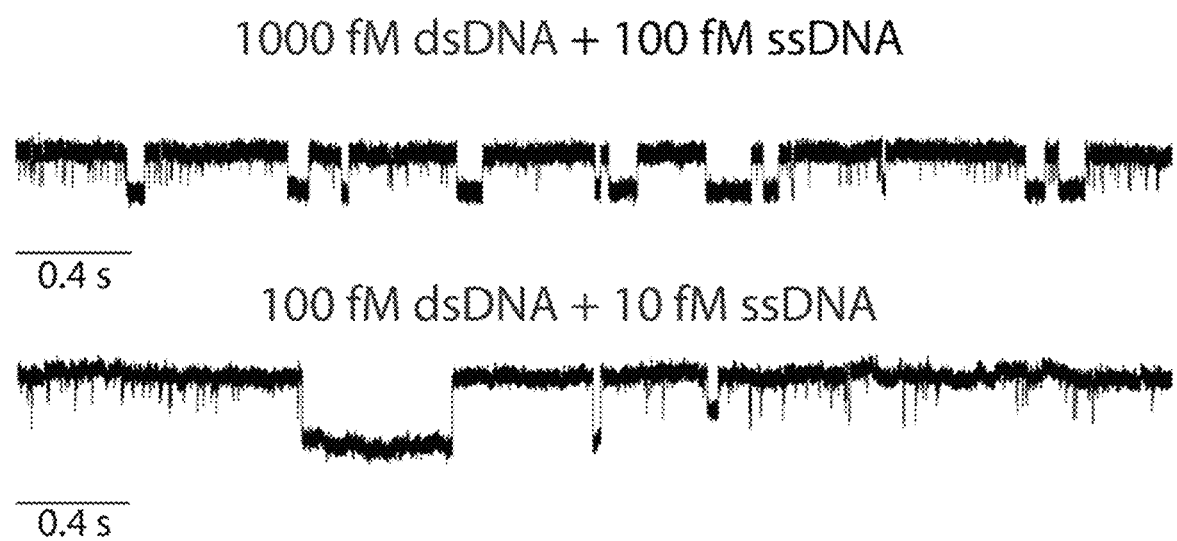

FIG. 19 illustrates example current recordings for the spiked dsDNA samples mixed with ssDNA with concentrations as indicated. This highly selective sensing does not come with a tradeoff in throughput as long as the ssDNA in the sample is below 10%. When the ssDNA in the sample is above 10%, their long translocation may start to reduce the throughput.

Figure 20:
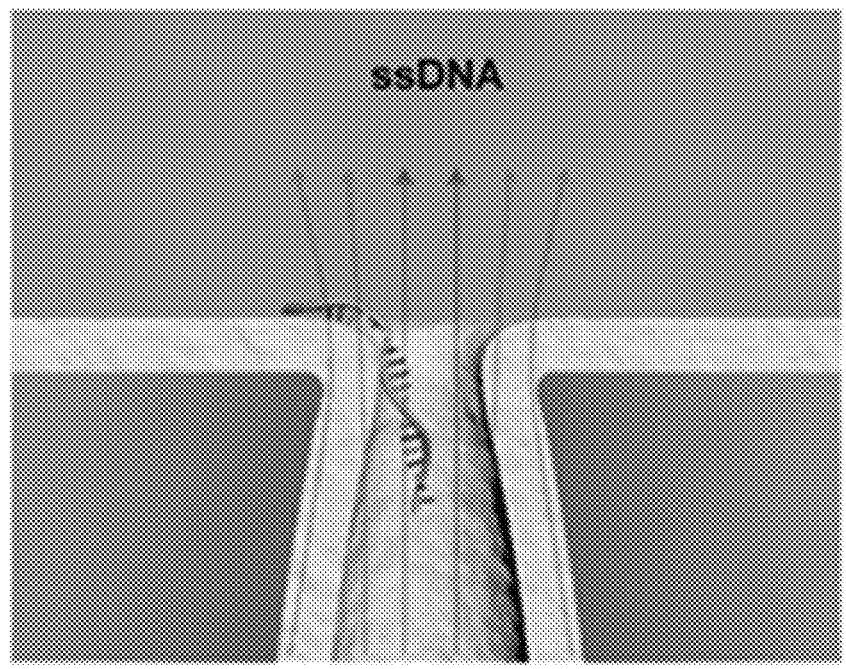

FIG. 20 is a schematic of 22 nt ssDNA translocation under the effect of electric field leakage. ssDNA molecules (persistence length, 2 nm) can easily deform and be pinned at the pore edge.

Figure 21:
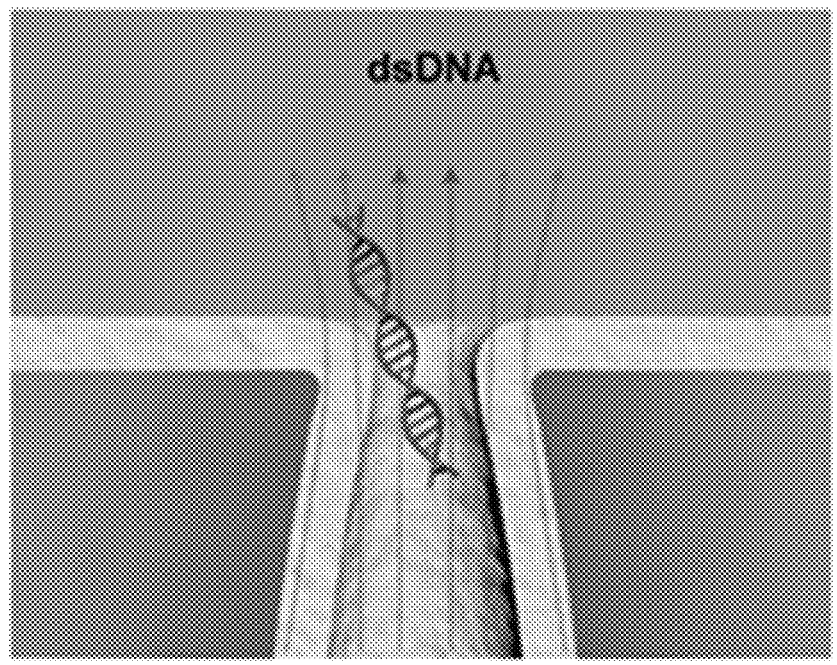

FIG. 21 is a schematic of 22 bp dsDNA translocation under the effect of electric field leakage. The stiffer dsDNA molecule (persistence length, 50 nm) tends to be linearly oriented under the influence of the strong local electric field and could be expected to have weak interactions with the leakage field.

Figure 22:
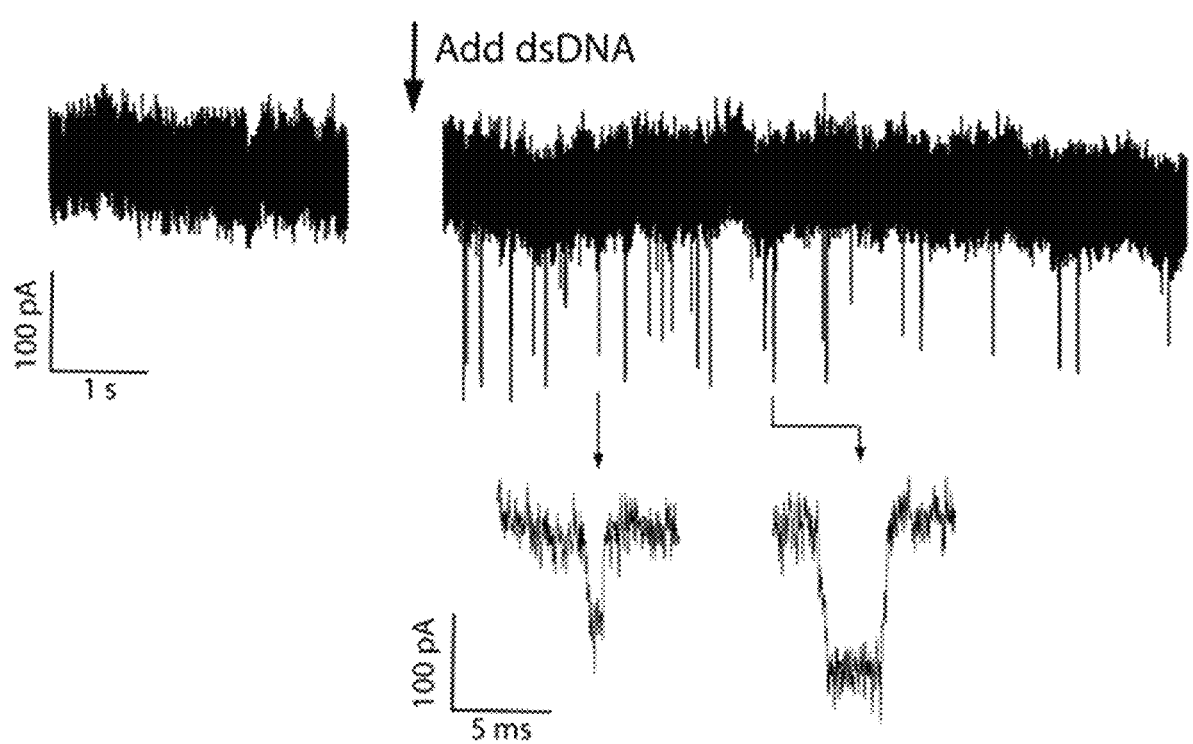

FIG. 22 illustrates example current recordings of 22 bp dsDNA translocation through bullet-shaped PET nanopores (10 nm, half cone angle ~7±2°) coated with 3 nm $Al_2O_3$ film under an applied voltage of 500 mV. Comparison between different solid-state nanopore platforms for short dsDNA translocation. Although this normal leakage field induced electrostatic interaction with dsDNA is not as strong as that for ssDNA, the translocation of short dsDNA through our nanopores with the presence of normal field leakage is still slower than that for other solid-state nanopores.

Figure 23:
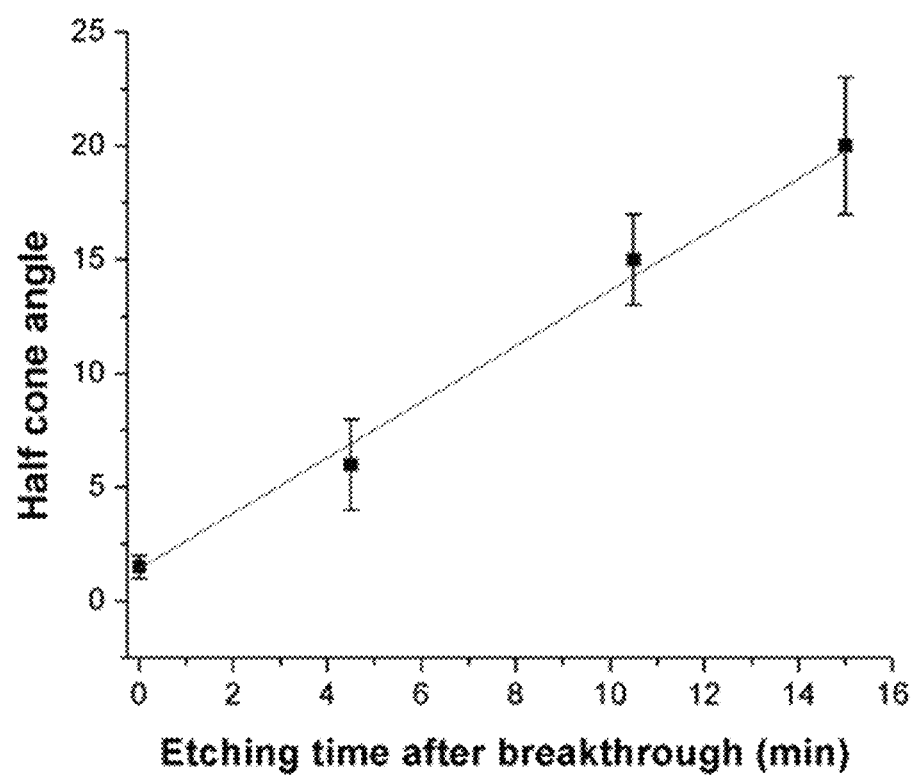

FIG. 23 graphically illustrates measured half cone angle of the asymmetric PET nanopore as a function of the time of etching under asymmetric conditions after breakthrough. The pore geometry evolves through a variety of configurations (half cone angles) with advancing time after breakthrough. While immediately after breakthrough the pore tips are trumpet-shaped, further etching is strongly affected by osmotic effects which eventually lead to bullet-shaped pore tips. Thus, asymmetric nanopores with different half cone angles can be fabricated by varying etching times after breakthrough.

Figure 24:
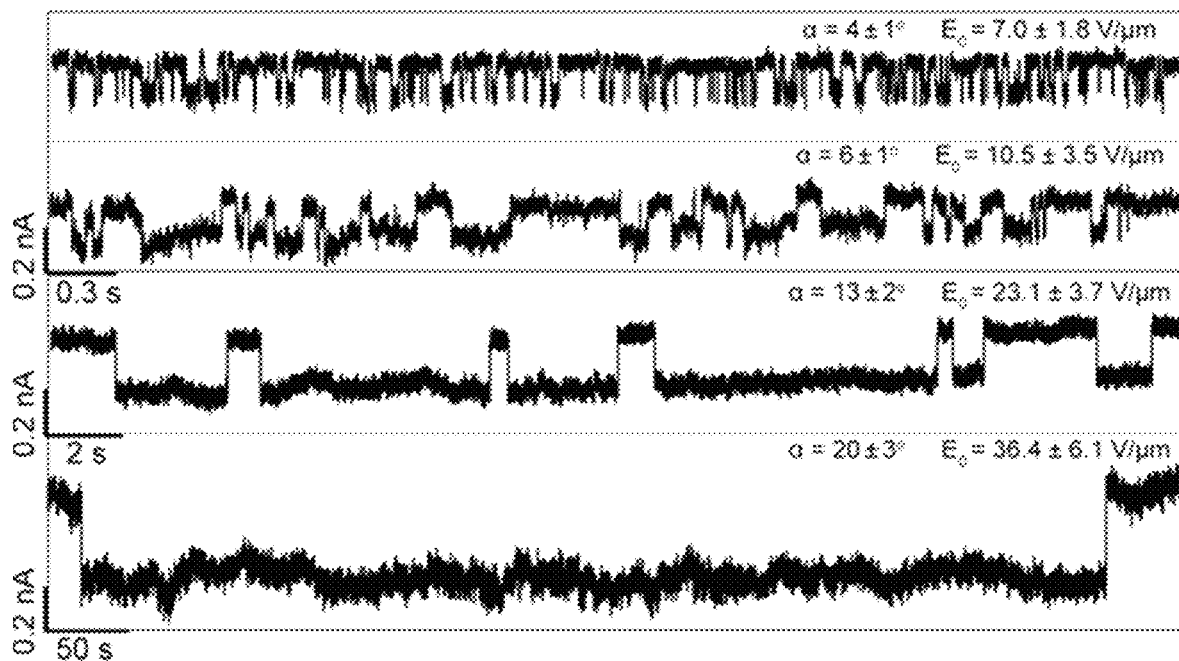

FIG. 24 illustrates representative current traces of 22 nt ssDNA translocating through four bullet-shaped $Al_2O_3$-coated (thickness, 3 nm) nanopores (diameter, 10 nm) with different half cone angles (a). The nanopores with larger cone angle allow more electric field ($E_0$, as indicated) to be focused at the nanopore tip under the same applied voltage (500 mV) and thus higher magnitude of normal leakage field at the pore edge. With the increase of half cone angle and thus normal leakage field, the average translocation time can be increased exponentially from milliseconds to hundreds of seconds.

Figure 25:
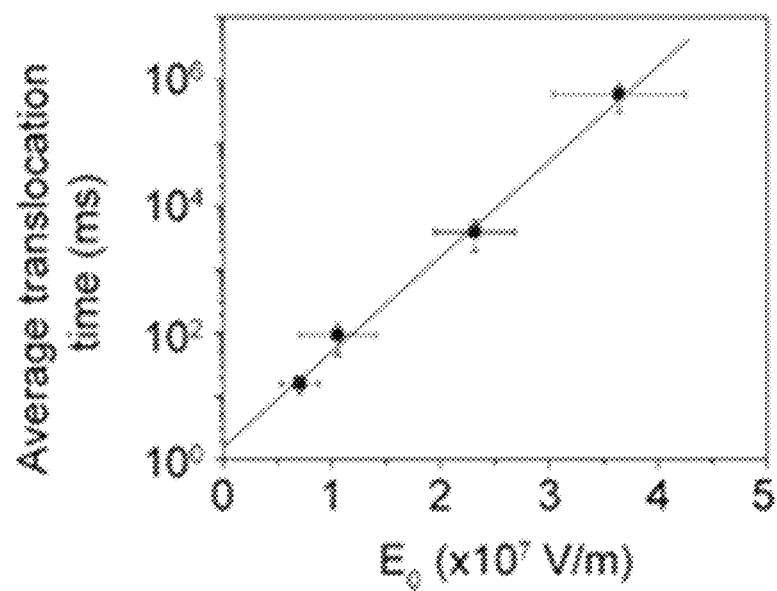

FIG. 25 graphically illustrates the average translocation time dependence of $E_0$. The line represents the fit of the data to the model.

Figure 26:
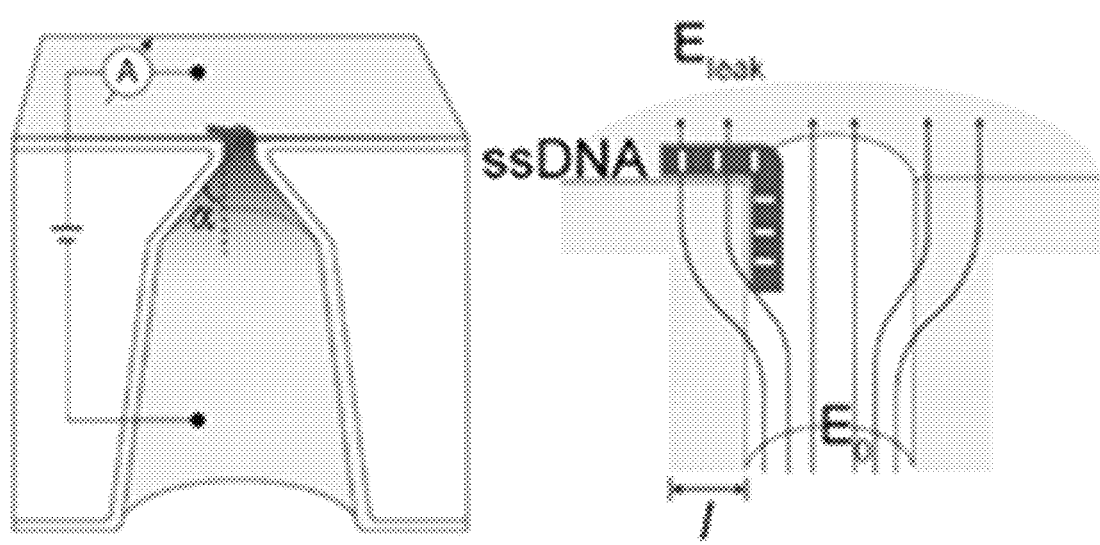

FIG. 26 is a schematic of the measurement apparatus using a bullet-shaped $Al_2O_3$-coated nanopores with a half cone angles of α (left); zoom in of the nanopore orifice with ssDNA electrostatically trapped at the pore edge by the normal leakage field (right).

Figure 27:

FIG. 27 illustrates an electrical recording of 22 nt ssDNA pinning at the pore edge under applied voltage of +500 mV (energy barrier, 12.7 kT) and ssDNA escaping from the nanopore after the electrostatic trapping effect is switched off by reversing the polarity of applied voltage to −500 mV.

Figure 28:
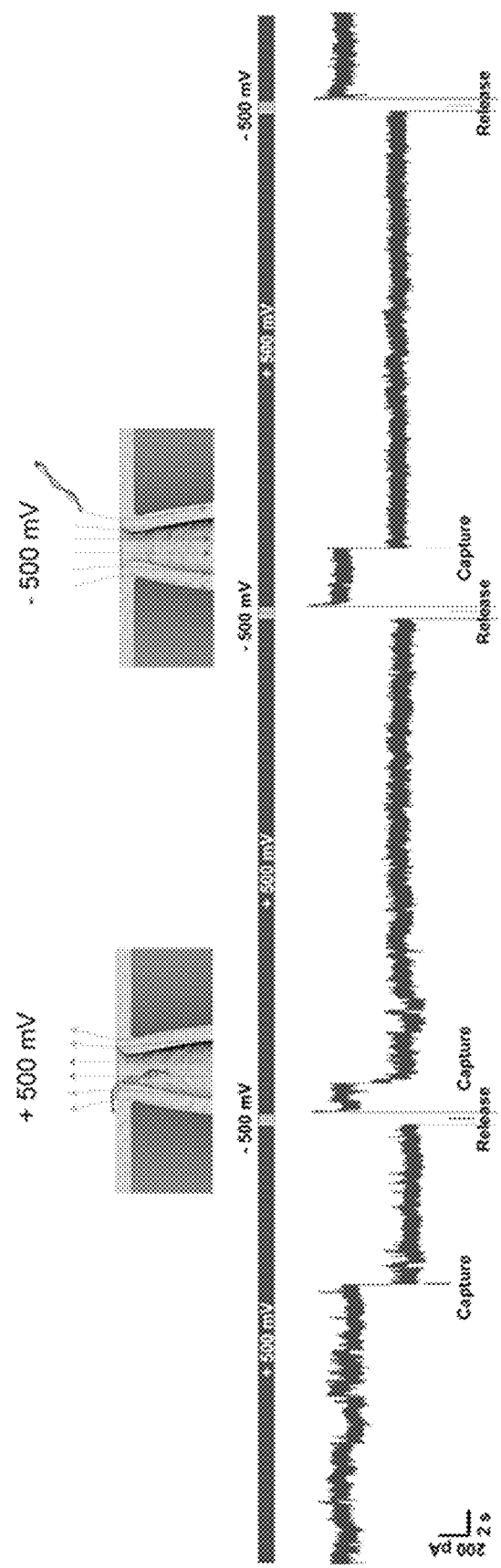

FIG. 28 illustrates continuous electrical recording of 22 nt ssDNA pinning at the pore edge under applied voltage of +500 mV (energy barrier, 12.7 kT) and ssDNA escaping from the nanopore after the electrostatic trapping effect is switched off by reversing the polarity of applied voltage to −500 mV. This electrostatic trapping effect is completely reversible.

Figure 29:
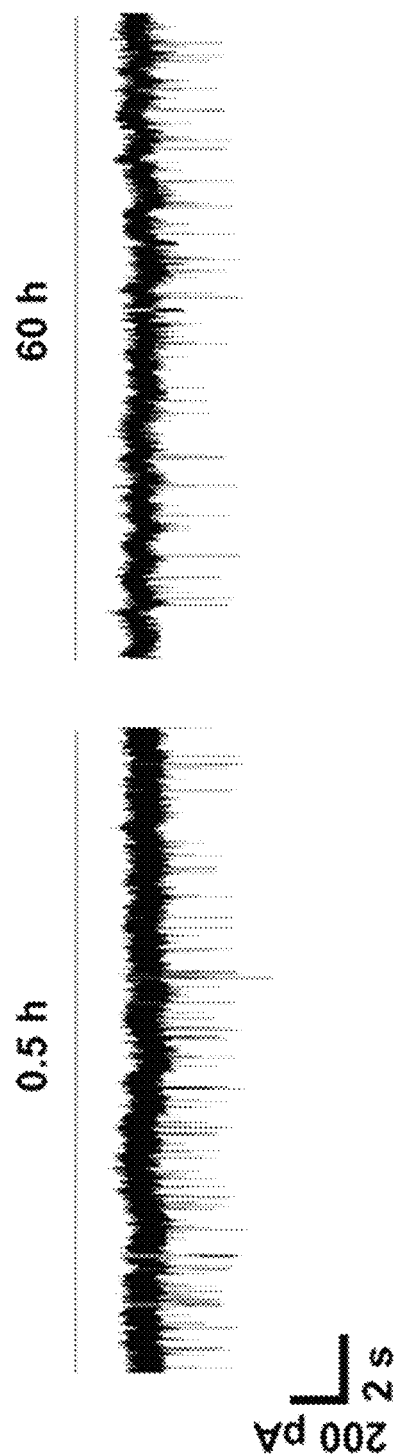

FIG. 29 illustrates a typical current versus time traces of 22 bp dsDNA translocation events. The reversible and selective electrostatic trapping effect confers non-fouling properties to these pores and enables resistive pulse recordings over several days without clogging. Both recordings are 20 s long; one was taken 0.5 h after addition of the sample and the other, 60 h later.

Figure 30:
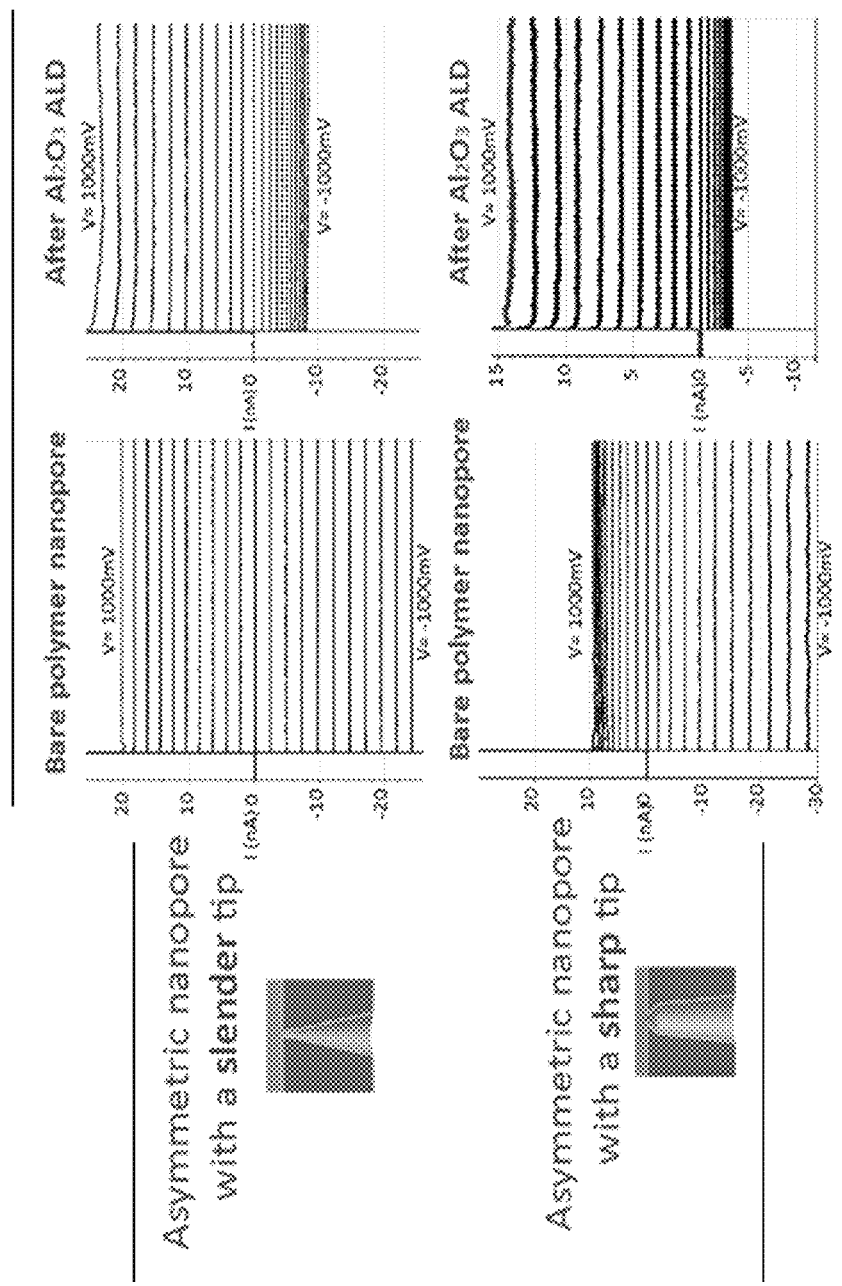

FIG. 30 illustrates ion current signals for asymmetric nanopores with a short slender tip or a sharp tip before and after the $Al_2O_3$ coating. The strong rectification effects under high ionic strength (1M KCl) indicate the field leakage phenomenon at the pore tip.

Figure 31B:
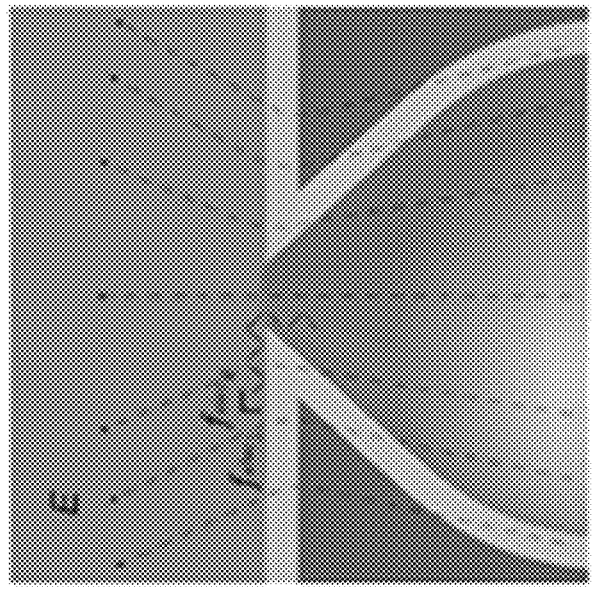
Figure 31A:
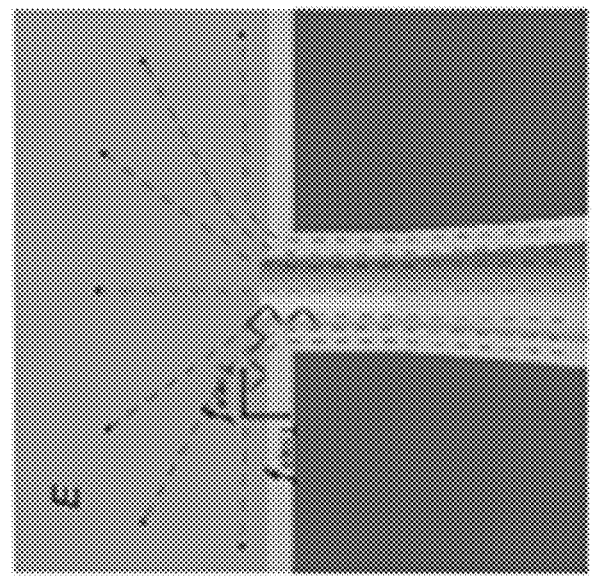

FIG. 31A is a schematic of single-stranded miRNAs translocating through a $Al_2O_3$ coated asymmetric nanopore with a slender pore tip.

FIG. 31B is a schematic of single-stranded miRNAs translocating through a $Al_2O_3$ coated asymmetric nanopore with a sharp pore tip.

Figure 31C:
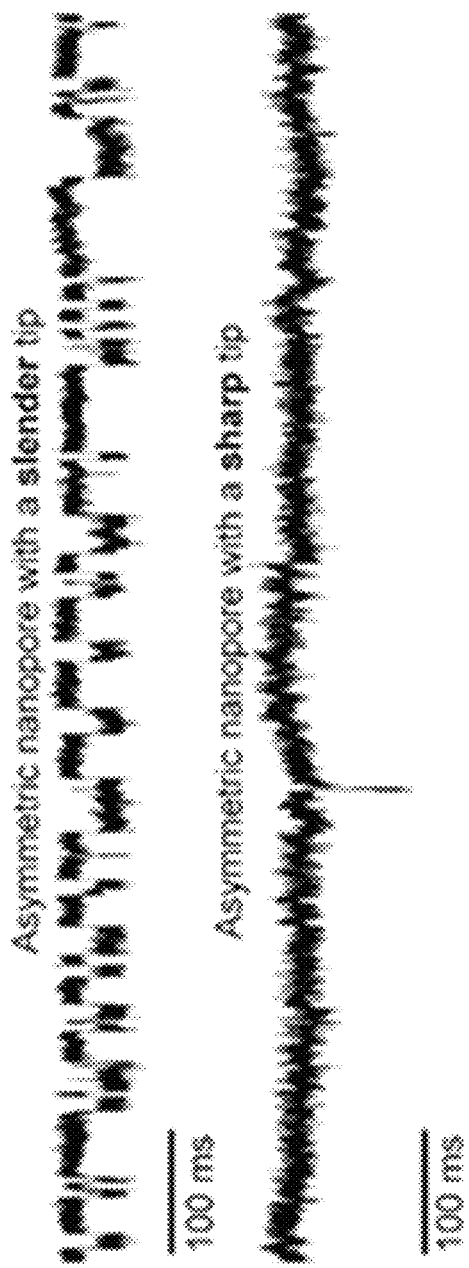

FIG. 31C illustrates electrical signatures of single-stranded miRNAs translocating through a $Al_2O_3$ coated asymmetric nanopore with a slender pore tip (top) or a sharp pore tip (bottom). For the asymmetric nanopore with a sharp tip, the electric field can also leak into the low-permittivity polymer which in turn decreases the normal field in the $Al_2O_3$ film and the tangential field to drive the molecule into the nanopore.

Figure 32A:
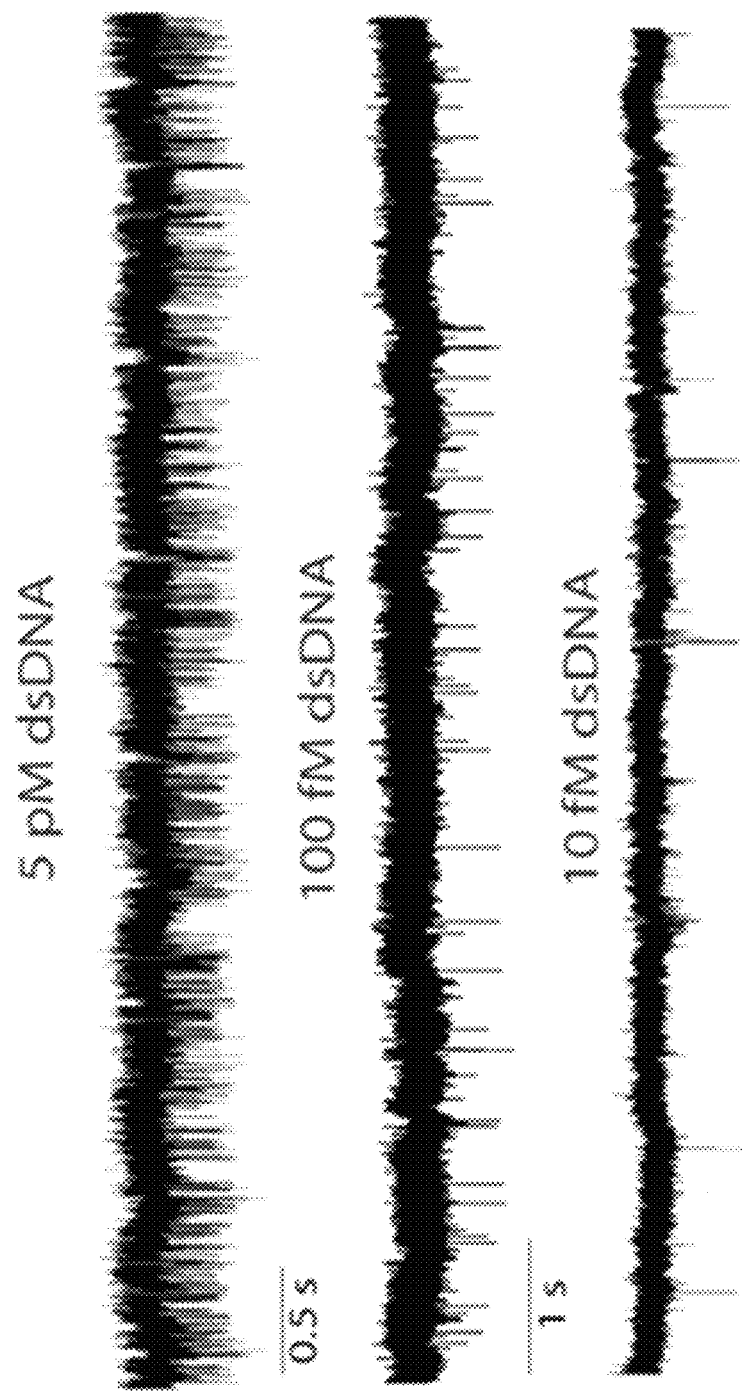

FIG. 32A illustrates example current recordings obtained using an $Al_2O_3$ nanopore with optimal pore shape and cone angle for the spiked dsDNA samples with three different concentrations (5 pM, 100 fM, 10 fM).

Figure 32B:
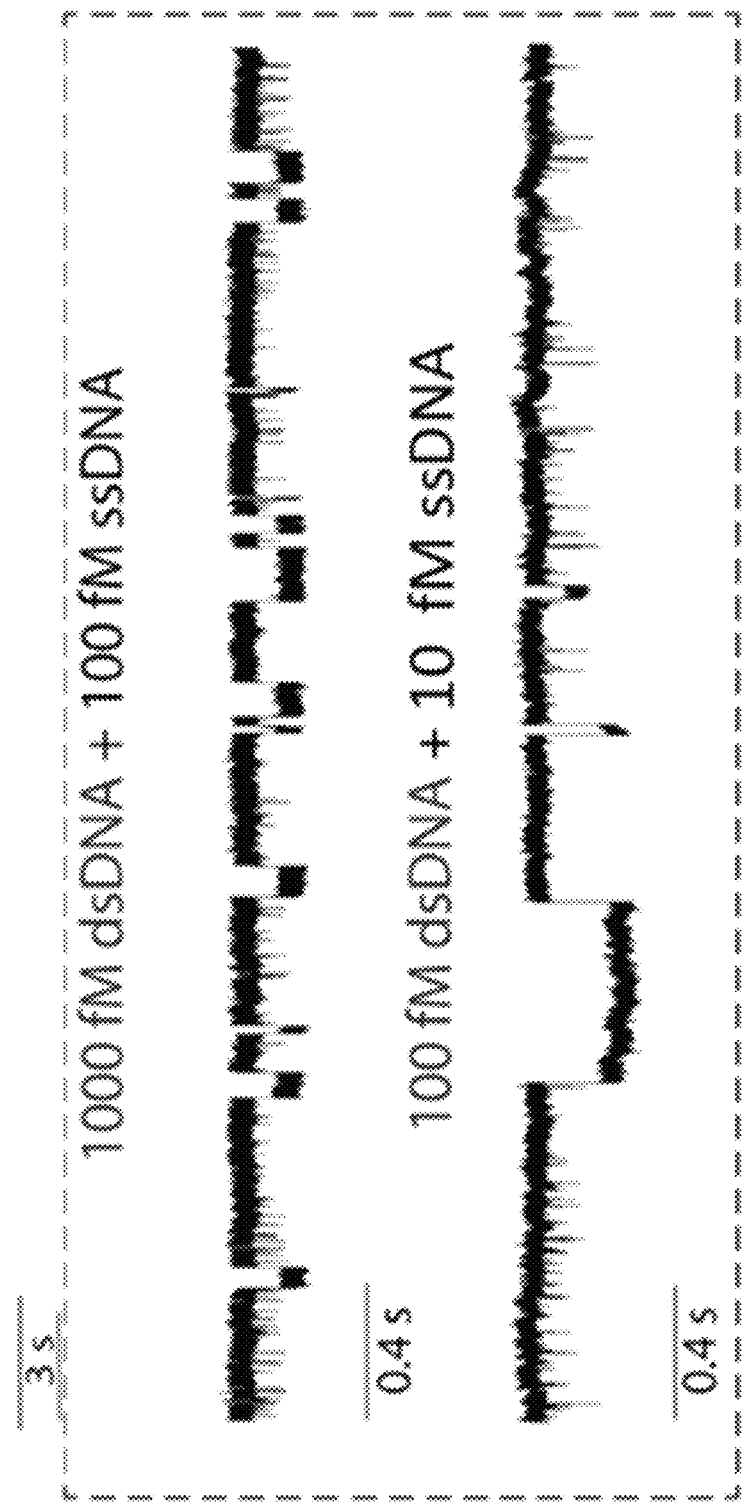

FIG. 32B illustrates example current recordings for the spiked dsDNA samples of FIG. 32A mixed with ssDNA.

Figure 32C:
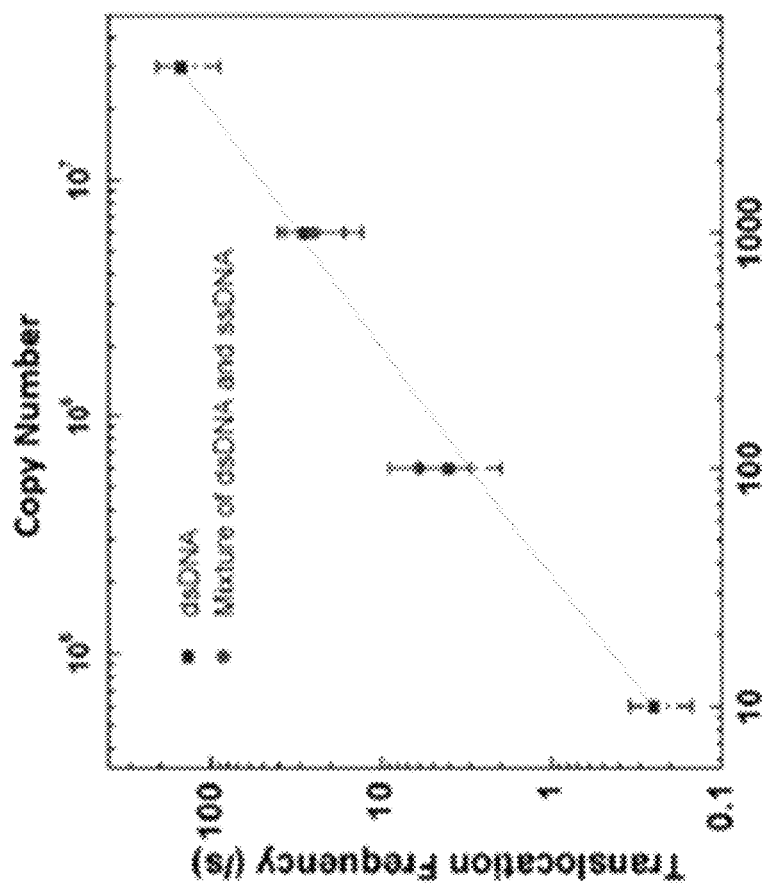

FIG. 32C graphically illustrates translocation frequency as a function of concentration. A bias of 500 mV was applied across the nanopore for all the experiments. The error bar for each translocation frequency data point indicates the pore to pore variations.

Figure 32D:
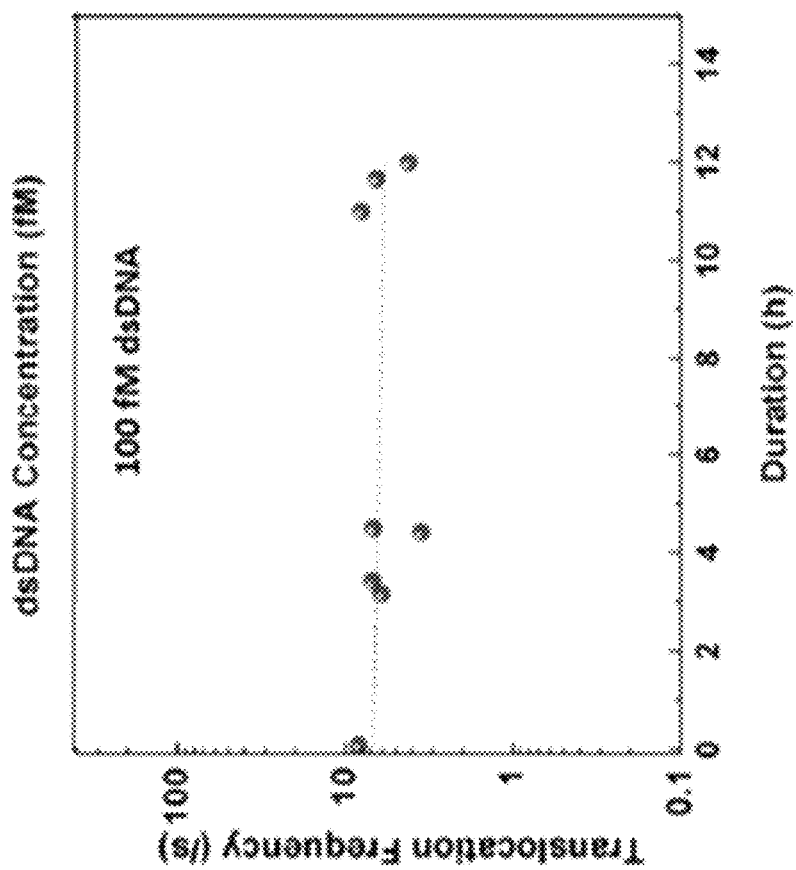

FIG. 32D graphically illustrates translocation frequency as a function of measuring duration. Note that the translocation frequency is obtained by using a 10 s moving window over 2-hour-long current trace data to find the maximum translocation frequency after filtering out current trace without significant event. For each nanopore, the variation of translocation frequency is less than 5%.

Figure 33:
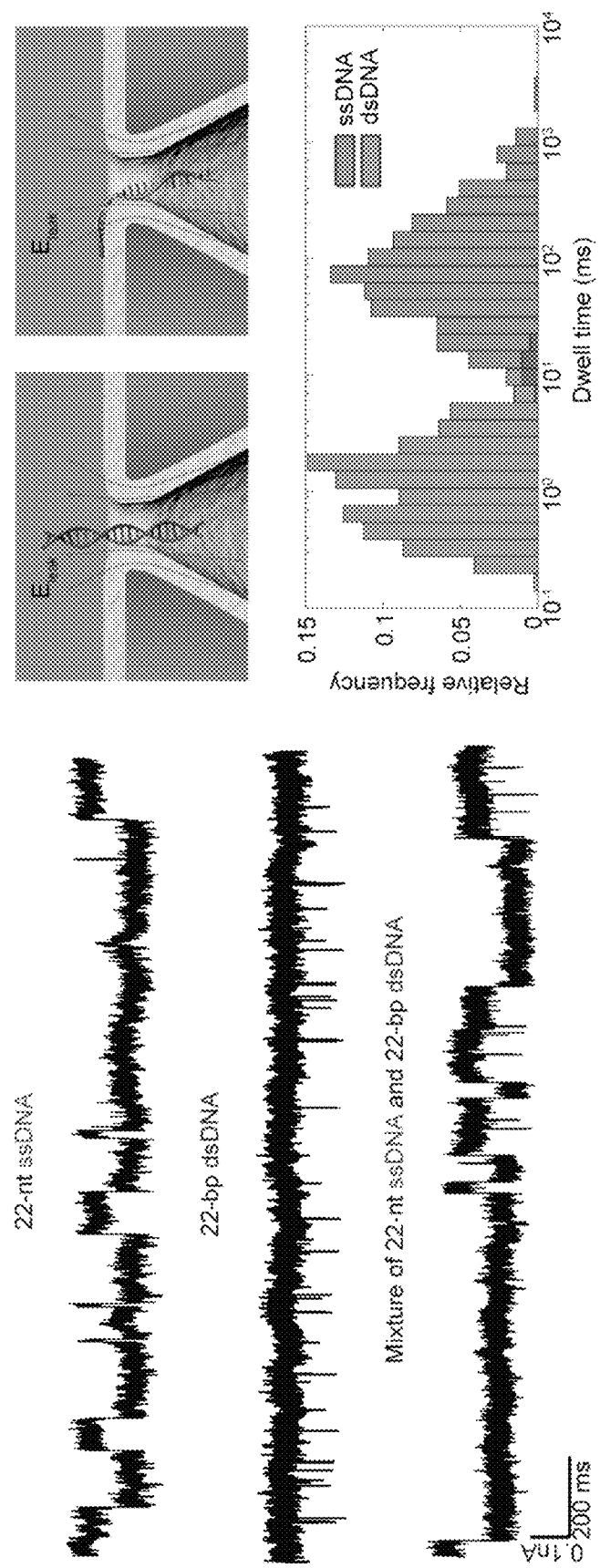

FIG. 33 illustrates 22 nt ssDNA and dsDNA translocation under the effect of electric field leakage. ssDNA molecules (persistence length, 2 nm) can easily deform and be pinned at the pore edge. While the stiffer dsDNA molecule (persistence length, 50 nm) tends to be linearly oriented under the influence of the strong local electric field and could be expected to have weak interactions with the leakage field.

Figure 34:
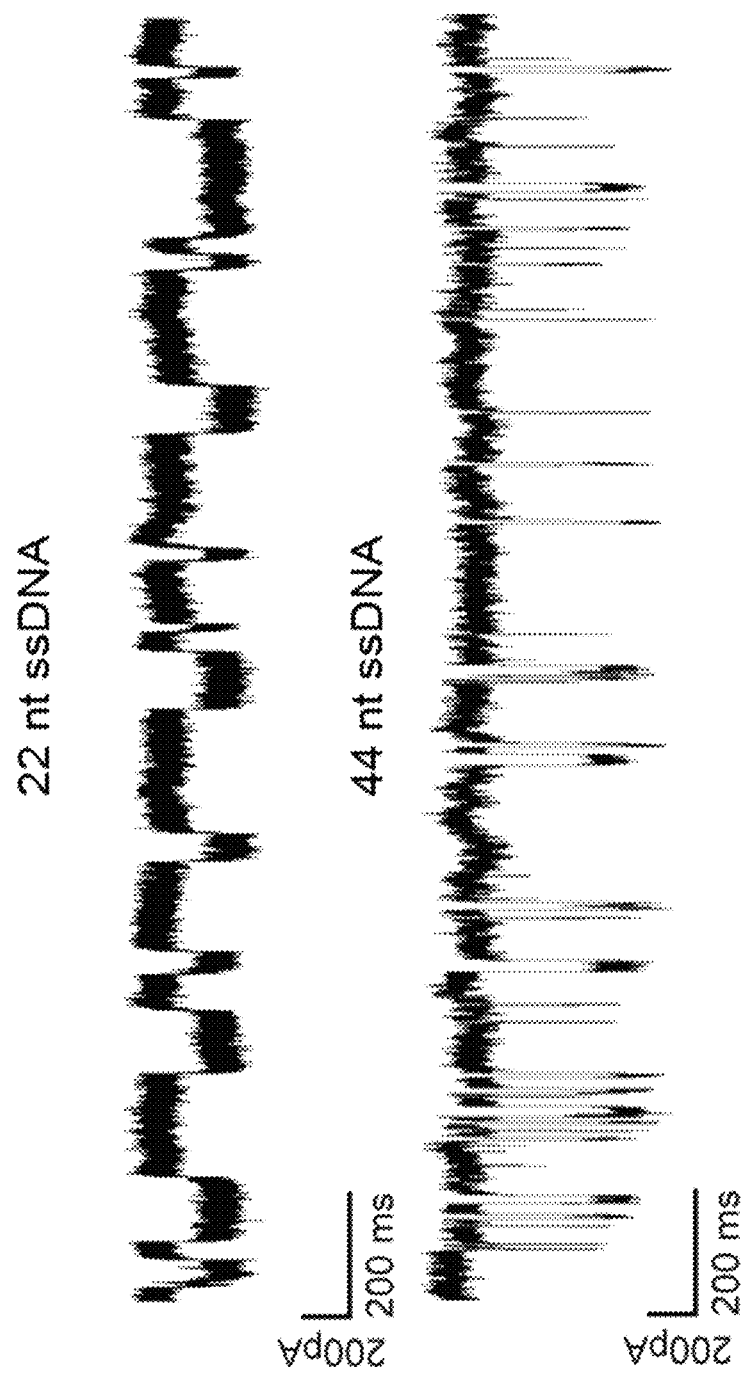

FIG. 34 illustrates distinct translocation signals of 22 nt ssDNA and 44 nt ssDNA under the effect of electric field leakage. The length dependence of translocation time and current magnitude can be used to design different molecular tags for specific multiplexed sensing.

DETAILED DESCRIPTION OF THE INVENTION

In a first aspect, the invention provides a system for detecting and quantifying a target single stranded polynucleotide. The system comprising: a membrane including a plurality of nanopores extending between a lower surface and an upper surface of the membrane. Each of the nanopores include a first opening and a second opening thereby defining a passageway through the membrane, a dielectric material coating the passageway and at least a portion of the upper surface. The passageway defines a first longitudinal axis and includes a first inner diameter at the first opening and a second inner diameter at the second opening, and the first diameter is smaller than the second diameter. The passageway diverges from the first opening to a first section of the passageway at a first slope and the passageway diverges from the first section to the second opening at a second slope. The first opening intersects the upper surface at the first inner diameter, and a second longitudinal axis, parallel to the longitudinal axis, intersects the first inner diameter and defines an angle with an adjacent inner surface of the passageway. The application of an electric field to the membrane traps the single stranded polynucleotide at the first opening.

Figure 1:
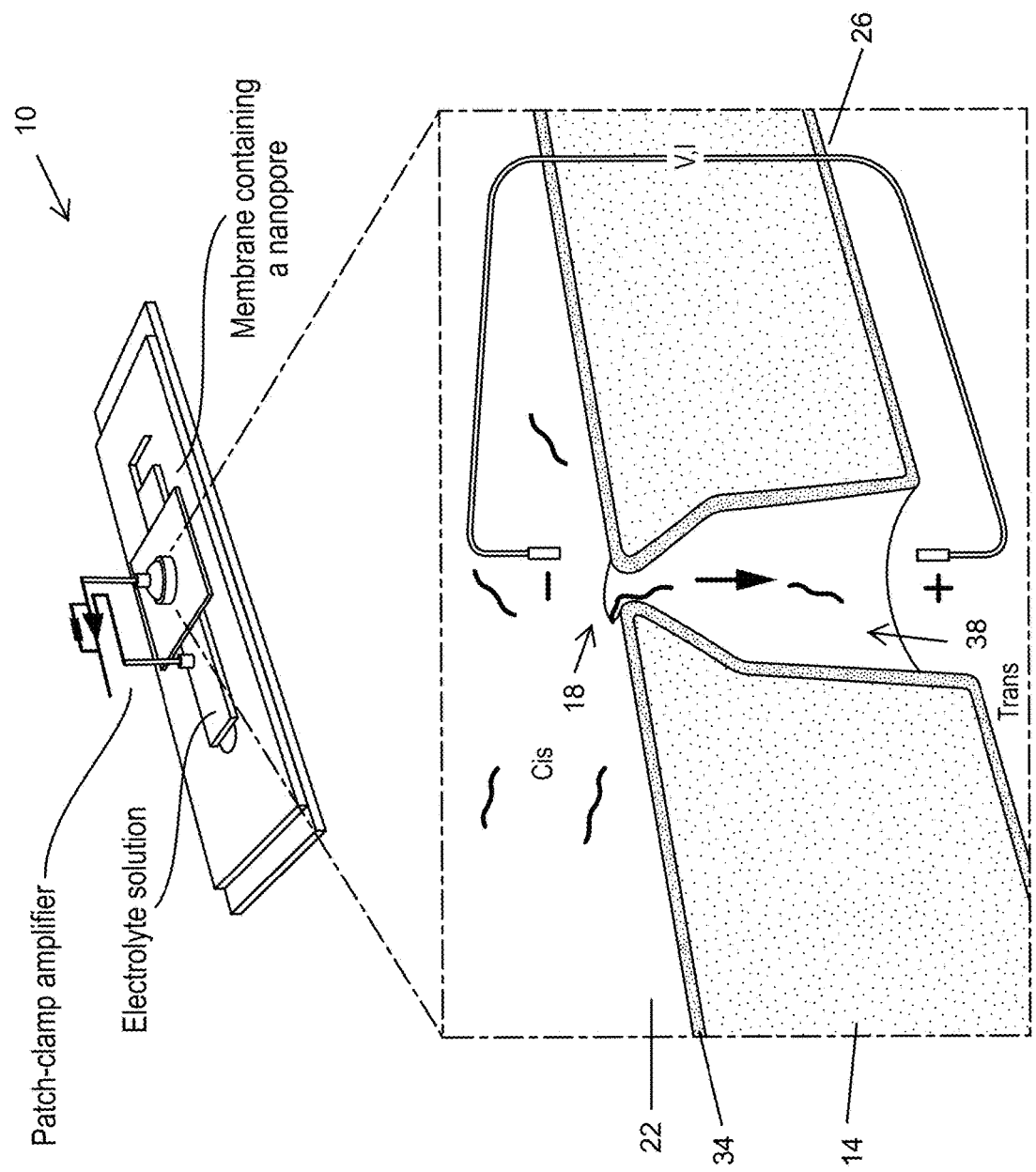
FIG. 1 is a schematic of a system for measuring resistive pulses from the translocation of individual single-stranded (ss) DNA through a single bullet-shaped polymer nanopore coated with a thin $Al_2O_3$ layer.

FIG. 1 illustrates a system 10 for controlling molecular translocation in solid-state nanopores by edge field leakage. The system dramatically reduces (by orders of magnitude) and controls the fast electrophoretic velocity of molecules to realize sensitive and selective solid-state nanopore sensors for polynucleotides and sequencing platforms. In particular, FIG. 1 schematically illustrates a set-up to measure resistive pulses from the translocation of individual single stranded polynucleotide, through a single nanopore. As illustrated in FIG. 1, an electric field is applied to a nanopore membrane. The electric field may be applied at a constant or a variable voltage and may be positively or negatively charged. Application of the electric field can be by any suitable means, including but not limited to electric fields from electrodes connected to a DC power supply, from an electromagnetic wave, or from piezoelectric surface vibrations. The electric field may be applied at between about 0.1 volts and about 1 volt. In one embodiment, the electrical field is between 400 mV to 600 mV. In another embodiment, the electrical field is about 500 mV.

Optical and electric intensity can become singular at metallic or dielectric cones or wedges. The singular tangential electric field at a 90-degree turn of an insulating wall is converted into a comparably singular leakage field across the corner by introducing finite wall permittivity. The leakage field exits the other side of the corner as an intense normal field that can arrest the transport of micro-colloids and trap them at the upstream side of the corner.

The systems and methods described herein comprise trapping the single stranded polynucleotide at the first opening. As used herein the term trap means to become immobilized and fail to continue to move through the nanopore passageway. The single stranded polynucleotide can be trapped temporarily for any length of time from nanoseconds to hours, or can be trapped permanently. In one embodiment, the single stranded polynucleotide is temporarily trapped and then release from the first opening. The single stranded polynucleotide can be released by any means including, but not limited to, applying a negative electric field to release the single stranded polynucleotide from the first opening, by heat/pH shock, pressure-driven flow, electrothermal flow, competing adsorption, ionic strength screening, etc.

As used herein, the singular forms "a", "an" and "the" include plural referents unless the context clearly dictates otherwise. "And" as used herein is interchangeably used with "or" unless expressly stated otherwise.

As used herein "single stranded polynucleotide," "polynucleotides" or "oligonucleotide" means at least two nucleotides covalently linked together. The polynucleotide may be DNA, both genomic and cDNA, RNA, or a hybrid, where the polynucleotide may contain combinations of deoxyribo- and ribo-nucleotides, and combinations of bases including uracil, adenine, thymine, cytosine, guanine, inosine, xanthine hypoxanthine, isocytosine and isoguanine. Polynucleotides may be obtained by chemical synthesis methods or by recombinant methods. Polynucleotides may be single stranded or may contain portions of both double stranded and single stranded sequence. The polynucleotides may also have a combination of single and double stranded portions wherein only a subset of the bases are engaged in complementary base-pairing. The depiction of a single strand also defines the sequence of the complementary strand. Thus, a polynucleotide also encompasses the complementary strand of a depicted single strand. Many variants of a polynucleotide may be used for the same purpose as a given polynucleotide. Thus, a polynucleotide also encompasses substantially identical polynucleotides and complements thereof. The polynucleotides may comprise 5 to 1000 nucleotides. For example, the polynucleotides may comprise 5 to 25 nucleotides, 10 to 50 nucleotides, 10 to 100 nucleotides, 10 to 250 nucleotides, 10 to 500 nucleotides, 100 to 1000 nucleotides, 250 to 1000 nucleotides, or 500 to 1000 nucleotides. In one embodiment, the polynucleotide contains 5-44 nucleotides.

Figure 2A:
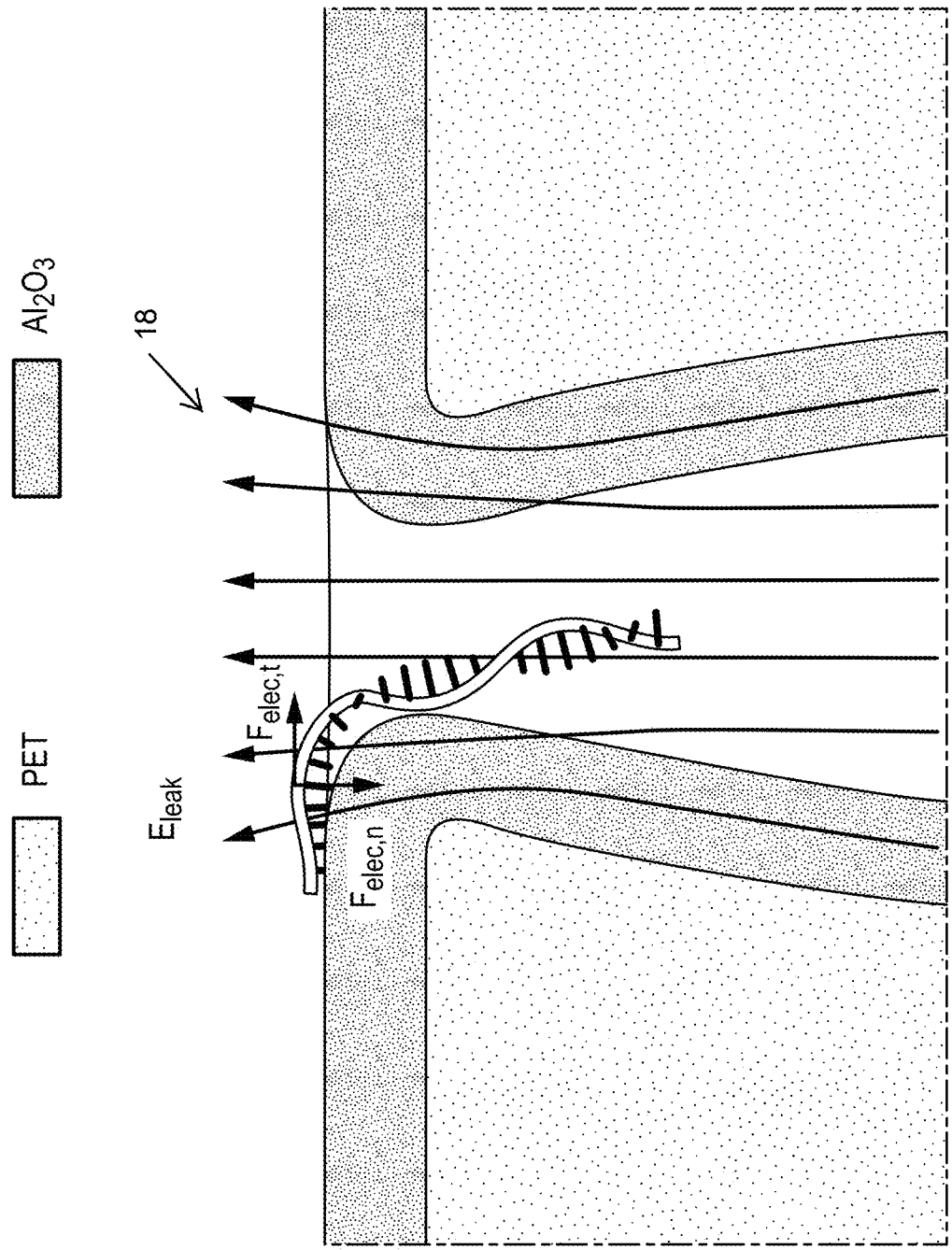
FIG. 2A is an enlarged portion of the system illustrated in FIG. 1.

With reference to FIGS. 1 and 2A, the system 10 includes a membrane 14 having one or more nanopores 18 formed therein. The membrane 14 includes a first surface 22 (e.g., top surface) and a second surface 26 (e.g., bottom surface). The membrane 14 can comprise a natural or synthetic material. Natural nanopores can comprise proteins. Synthetic membranes can comprise any suitable material(s), including but not limited to a polymer, polymer mixture (polyethylene terephthalate (PET), polycarbonate (PC), Polypropylene (PP), and/or Polyimides (PI)). In one embodiment, the polymer is PET. In another embodiment, the polymer is PI. In one embodiment, the membrane comprises an insulative material. In other embodiments, the insulative polymer can comprise PC or PP.

The nanopores 18 extend between the first surface 22 and the second surface 26. FIGS. 1-2A illustrate a single nanopore 18, however it should be understood that additional nanopores 18 can be formed within the membrane 14. In one embodiment, the membrane contains between 1 and $1\times10^8/$cm$^2$ number of nanopores. The nanopore can be any size suitable for use in the current invention. In one embodiment, the nanopore has a radius of between 5 nm and 500 nm. The nanopore can also be any shape suitable for use in the invention, including, but not limited to: conical or cylindrical, bullet-shaped or trumpet-shaped and can be symmetrical or asymmetrical. The nanopore openings/tips can also be any shape, both symmetrical and asymmetrical.

The existence of the nanopore from the lower surface 22 to the upper surface 26 creates a passageway 38. The system 10 includes a dielectric material 34 that covers at least a portion of the membrane 14 and the passageway 38. The amount of the membrane 14 coated by the dielectric material can be any amount, including, but not limited to both the upper 26 and lower 22 surfaces.

The passageway 38 is coated with the dielectric material 34. The dielectric material can comprise any suitable materials including, but not limited to Al$_2$O$_3$, SiN, SiO$_2$, HfO$_2$, hafnium silicate, zirconium silicate, and/or zirconium dioxide. In one embodiment, the dielectric material is Al$_2$O$_3$. In one embodiment, the dielectric material 34 has a thickness that can range from 1 nm to 10 nm. In another embodiment, the dielectric material 34 has a thickness that can range from 2 nm to 5 nm. In yet another embodiment, the dielectric material 34 has a thickness of 3 nm.

As further illustrated in FIGS. 2A-2B, the dielectric material 34 covers the first surface 22, the second surface 26, and the nanopore 18. The dielectric coated nanopore 18 defines a passageway 38 including an inner surface 42. The dielectric material 34 has a high permittivity to produce a high normal leakage field that can trap the polynucleotides on the inner surface 42 of the nanopore 18. In one construction, the coating is Al$_2$O$_3$. The leakage normal field is comparable in intensity as the translocation field. It is yet sufficiently weak to prevent permanent trapping of the molecules (and clogging of the nanopores 18) such that they are able to unpin with an activated escape that is molecule specific. Since the leakage field is outside the membrane 14, it does not interfere with the resistive signal current from within the nanopore 18. FIG. 2A further illustrates the field leakage through the nanopore transition entrance (discussed below).

With continued reference to FIGS. 1 and 2B, the nanopore 18 is generally bullet-shaped and includes a first opening 46 through the first surface 22 and a second opening 50 through the second surface 26. The passageway 38 extends between the first opening 46 and the second opening 50 and defines a first longitudinal axis 54 extending through the first opening 46 and the second opening 50. The first opening 46 includes a first inner diameter D1, and the second opening 50 includes a second inner diameter D2. As illustrated in the figures, the first inner diameter D1 is smaller than the second inner diameter D2. In one embodiment, the first inner diameter D1 can range from 4 nm to 50 nm. In another embodiment, the first inner diameter D1 can range from 5 nm to 20 nm. In yet another embodiment, the first inner diameter D1 is 8 nm. In one embodiment, the second diameter D2 can range from 50 nm to 600 nm. In another embodiment, the second inner diameter D2 can range from 100 nm to 500 nm. In yet another embodiment, the second inner diameter D2 is 400 nm.

The passageway 38 diverges from the first opening 46 to a first section 58 of the passageway 38 at a first slope S1 and continues to diverge from the first section 58 to the second opening 50 at a second slope S2. The first slope S1 can range from 2° to 30°. The first slope S1 may vary and is not required to be constant over the entire length between the first opening 46 to the first section 58. The second slope S2 can range from 1° to 20°. Similarly, the second slope S2 may vary and is not required to be constant over the entire length between the first section 58 and the second opening 50.

The first opening 46 includes a transition area 48 from the first surface 22 into the passageway 38. The transition area 48 provides a contoured (e.g., no sharp edges) surface and includes the first inner diameter D1, which is the smallest inner diameter in the passageway 38. The inner diameter of the passageway 38 gradually increases when moving from the first inner diameter D1 toward the second opening 46 where the second inner diameter D2 is largest.

A second longitudinal axis 62 is shown in FIG. 2B. The second longitudinal axis 62 is parallel to the first longitudinal axis 54 and intersects the inner surface 42 of the passageway 38 at the first inner diameter D1. This intersection defines an angle 66 (e.g., a cone angle) between the inner surface 42 of the passageway 38 and the second longitudinal axis 62. In one embodiment, the angle 66 can range from 4 degrees to 20 degrees. In another embodiment, the angle 66 can range from 5 degrees to 10 degrees. In yet another embodiment, the angle 66 is 9° degrees.

As illustrated in FIGS. 1, 2A, and 2B, the nanopore 18 includes a generally conical base and a short straight nanopore at the first opening 46. The generally conical base with the membrane wall focuses the electric field, and the dielectric material 34 on the straight nanopore transition area 48 facilitates field leakage at the first opening 46.

Once the field lines enter the dielectric material 34 inside the nanopore, the axially conditioned parallel field lines within the straight nanopore transition area 48 ensures that the field intensity in the dielectric material 34 is identical to that in the aqueous phase in the nanopore, despite the higher permittivity of the latter phase.

In a further aspect the invention provides a method of delaying translocation of a target single stranded polynucleotide, comprising applying an electric field to a membrane having a nanopore edge to enhance a leakage field. The membrane includes a plurality of nanopores extending between a lower surface and an upper surface of the membrane. Each of the nanopores include a first opening and a second opening thereby defining a passageway through the membrane with a dielectric material coating the passageway and at least a portion of the upper surface. The passageway defines a first longitudinal axis and includes a first inner diameter at the first opening and a second inner diameter at the second opening. The first inner diameter is smaller than the second inner diameter. The passageway diverges from the first opening to a first section of the passageway at a first slope and the passageway diverges from the first section to the second opening at a second slope. The first opening intersects the upper surface at the first inner diameter, and a second longitudinal axis, parallel to the first longitudinal axis, intersects the first inner diameter and defines an angle with an adjacent inner surface of the passageway, temporarily trapping the target single stranded polynucleotide at the first opening.

Variations in the applied electric field voltage can be used to vary the translocation time for the single stranded polynucleotides through the nanopore passageway.

Additionally, the duration of trapping is a function of the length, flexibility and molecular tags (nanobeads, proteins, etc.) of the single-stranded DNA or RNA. The different ssDNAs or RNAs can be differentiated based on the trapping duration. The translocation time of the molecule depends on its flexibility and conformation which are a function of its length relative to its persistence length. The persistence length changes dramatically when a single-stranded DNA hybridizes with its complementary oligonucleotide to form a double-stranded complex. It can also be changed with protein, nanoparticles and other molecular tags. This offers a way to specifically identify target molecules through their hybridization complexes. See FIGS. 33-34.

The methods described herein comprise delaying translocation of the single stranded polynucleotide. As used herein delaying translocation is defined as preventing or slowing movement of the single stranded polynucleotide thought the nanopore passageway. Translocation can take between 1 ms-$10^4$ ms. In one embodiment, the translocation time is slowed to between 10-10,000 ms.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

EXAMPLE 1

Fabrication of $Al_2O_3$-Coated Polymeric Nanopore

The 12 μm thick polyethylene terephthalate (PET) foils were irradiated with single swift heavy ions (Au) with energy of 11.4 MeV per nucleon at the GSI in Darmstadt, Germany. An irradiated foil was subsequently etched at room temperature (295 K) by an asymmetric etching method, where the foil was mounted between two isolated containers that contained an etchant solution of 2.5 M NaOH in 1:1 MeOH/$H_2O$ and a stopping solution of 1 M HCOOH and 1 M KCl aqueous solution, respectively. The etching process started from one side of the PET foil, but was immediately stopped when etched through, and as a result, a single trumpet-like nanopore was formed on each irradiated PET foil. Bullet-shaped nanopores with different half cone angles were fabricated following an extended asymmetric etching procedure. To improve the control of nanoscale morphology at the nanopore tip, the track-etched polymer nanopore etching method was optimized as shown in Table 1. In all cases, the radius of the base was around 500±80 nm, as determined by electron microscopy. The final tip radius was determined by an electrochemical method. Thermal ALD $Al_2O_3$ films of 3 or 10 nm were grown in a commercial (Cambridge Nanotech, Savannah S100) ALD reactor using trimethylaluminium (TMA) and de-ionized (DI) water as precursors. A low deposition temperature of 110 ° C. was chosen to prevent thermal damage to the polymer PET.

TABLE 1

Comparison of conventional and optimized polymer nanopore etching methods

| | Conventional method | Optimized method | Remarks |
|---|---|---|---|
| Storage | In Air | In $N_2$ | Reduce the air exposure can minimize the $O_2$ sensitization effect on the track and thus sample to sample variation |

TABLE 1-continued

Comparison of conventional and optimized polymer nanopore etching methods

| | Conventional method | Optimized method | Remarks |
|---|---|---|---|
| UV Sensitization | Yes | No | Maintain the low-permittivity property of polymer membrane by skipping UV irradiation step |
| Chemical etching recipe | One step asymmetric etching: 9M NaOH:1M HCOOH | Three step etching: 1$^{st}$: 2.5M NaOH:0.5 HCOOH in DI and methanol (1:1) 2$^{nd}$: 1M NaOH:0.5M HCOOH in DI and ethanol (1:1) 3$^{rd}$: 2M HaOH:2M NaOH | Divide the etching into three steps, in 1$^{st}$ step, strong etchant is applied to etch through the asymmetric nanopore. In 2$^{nd}$ step, weaker etchant is used to fine-tune the pore tip cone angle. In 3$^{rd}$ step, mild symmetric etchant condition is applied to fine-tune the pore tip size while maintaining a slender pore tip |

Experiment of DNA Transport

A PET foil with a single $Al_2O_3$-coated polymeric nanopore was mounted between two isolated channels that were both filled with buffered 1 M KCl aqueous solution (0.01× PBS, pH=7.4). A patch clamp amplifier (Axopatch 200B, Molecular Devices Inc.) with Ag/AgCl electrodes was used to measure the current trace and the current-voltage response across the nanopore. The polarity of the applied voltage was referenced to the tip side electrode. The current data were collected at 50 kHz with a low-pass Bessel filter of 10 kHz. For the DNA transport experiment, the buffered 10 pM 22 nt ssDNA and 22 bp dsDNA (Integrated DNA Technologies) solution (in 1 M KCl, 0.01× PBS, pH=7.4) was always freshly made prior to each experiment and was injected to the tip side of the nanopore. 22 bp dsDNA was obtained by hybridizing two complementary oligos and then purified by gel electrophoresis. Unless otherwise specified, a positive voltage of 500 mV was used in the transport experiment to drive the negatively charged molecules through the nanopore from tip to base.

The Electric Field Leakage Phenomenon in Nanopores

Figure 3:
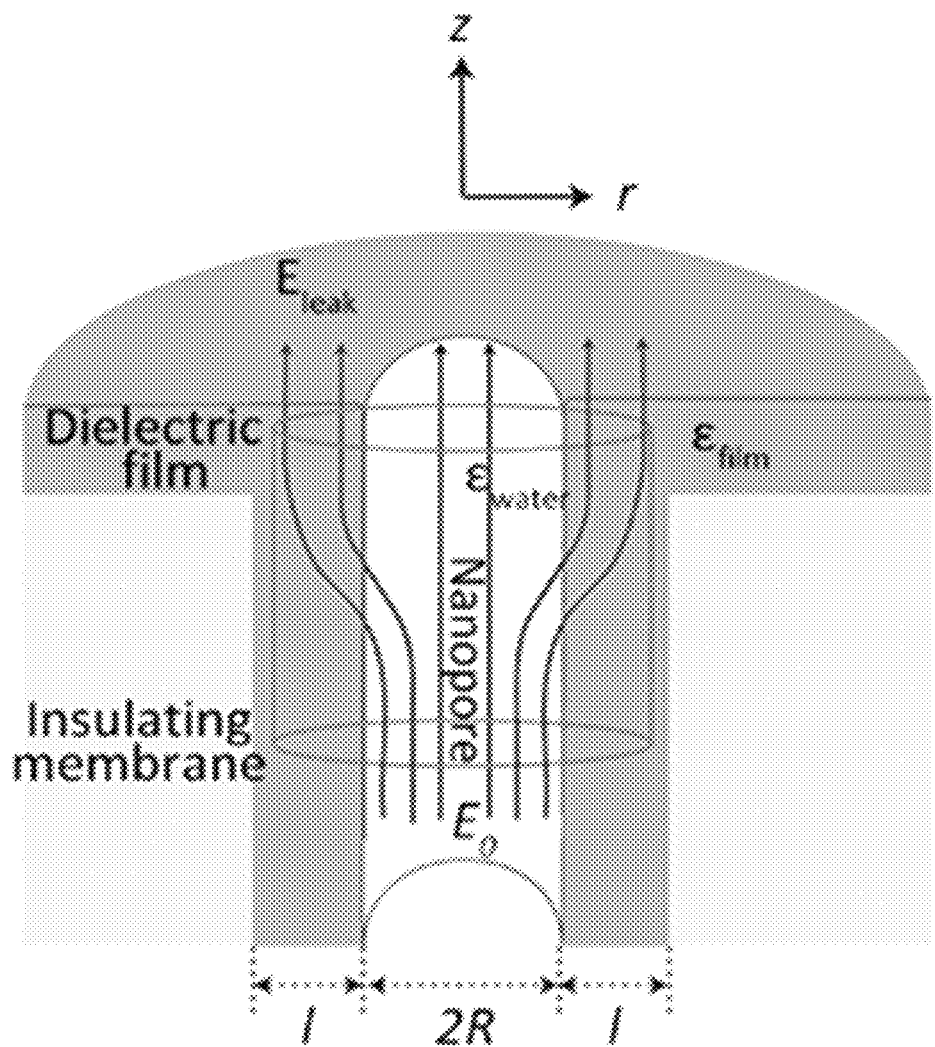
FIG. 3 is a schematic of a solid-state nanopore orifice in an insulating membrane coated with high-permittivity dielectric films and Gauss volume.

The solid-state nanopore has a conical base and a short straight portion at the tip, as illustrated in FIGS. 1 and 2A-B. The conical base with the insulating PET membrane wall focuses the electric field and the high-permittivity $Al_2O_3$ film on the straight nanopore edge facilitates field leakage at the tip end. Once the field lines enter the dielectric material 34 inside the pore, the axially conditioned parallel field lines within the straight pore transition area 48 ensures that the field intensity in the dielectric material 34 is identical to that in the aqueous phase in the pore, despite the higher permittivity of the latter phase. With the converging geometry at the conical base, the field lines are confined to the aqueous bulk. A simple Gauss volume flux balance then relates the normal leakage field $E_{leak}$ and the average electric field $E_0$ in the pore entrance at the neck with the conical base as illustrated in FIGS. 3-4.

$$E_{leak} = \frac{\varepsilon_{film} E_0 R^2}{\varepsilon_{water} R^2 + \varepsilon_{film}((R+l)^2 - R^2)} \quad (1)$$

where $\varepsilon_{water}$ and $\varepsilon_{film}$ are the permittivity of water and dielectric film, respectively, R is the radius of the pore orifice, and l is the thickness of the dielectric film 34. Two limits of equation (1) are instructive. For l/R approaching infinity, corresponding to a non-polymeric dielectric membrane whose area is much larger than the pore tip area, $E_{leak}/E_0$ scales as $(R/l)^2 \ll 1$. This indicates conventional solid-state nanopores fabricated in dielectric membranes (such as SiN, $SiO_2$ and $Al_2O_3$, etc.) cannot produce significant molecule-pinning field at the pore edge as the field is distributed over a large surface area that scales as $l^2$. To date, there has been no experimental report of prolonging translocation times in dielectric membrane nanopores by edge field leakage. In fact, this field penetration across the entire dielectric membrane causes significant dielectric noise in the nanopores. The other limit of l/R approaching zero yields that $E_{leak} \sim E_0(\varepsilon_{film}/\varepsilon_{water})$. The leakage field would then be proportional to the applied field and of comparable intensity if the permittivity ratio is not too small. Therefore, a compound pore, with a nearly insulating polymer membrane and a thin high-permittivity dielectric film, is necessary for a leakage field with intensity and dimension that can delay the molecular translocation time without generating significant noise in the resistive signal.

A single nanopore was fabricated with an asymmetric shape in polyethylene terephthalate (PET) membranes by the track-etching method and subsequently an $Al_2O_3$ dielectric film was deposited on the pore wall by Atomic Layer Deposition (ALD). The strength of the electric field at the pore tip was fine-tuned through the choice of cone angles under the same applied voltage. The as-fabricated nanopores with large cone angles have a bullet-like shape while nanopores with small cone angles have a trumpet-like shape. See FIGS. 5A-B, which illustrate SEM characterization of nanopores. FIG. 5A is a schematic illustration (not to scale) and cross-sectional SEM images of a trumpet-like nanopore (left) after etching breakthrough and a bullet-like nanopore (right) after extended etching. Scale bar=400 nm. FIG. 5B are representative SEM images of the tip side (top) and the base side (bottom) of an ALD $Al_2O_3$ coated polymeric nanopore. Scale bar=500 nm. PET is highly insulating and has been used as a supporting substrate to significantly reduce the dielectric noise of nanopores in dielectric membranes. $Al_2O_3$ has a large dielectric constant of 8. ALD offers precise control of nanoscale film thickness.

Finite-element COMSOL simulations confirmed that the electric field intensity within the dielectric film increases considerably and develops a normal field leakage when approaching the pore transition area (FIG. 6). In FIG. 7, the intensity of normal leakage field along the r axis is shown for different film thicknesses l (3-50 nm). The rapidly increasing (singular) intensity of normal field at the pore transition area with decreasing l confirms enhanced field leakage in PET nanopores coated with a thin $Al_2O_3$ film. The zero thickness limit is singular, as the field at the pore transition area would be purely tangential for a perfectly insulating membrane.

A way to experimentally verify the presence of field leakage at the pore transition area is to measure the rectification of the ionic current. The leakage field enters the $Al_2O_3$ film within the pore and can induce intra-pore dielectric polarization and different charge on the pore surface when the voltage bias is inverted. The strength of the induced surface charge depends on the leakage field, which is sensitive to the pore geometry and film thickness. At a sufficiently high voltage, this mechanism can produce ionic current rectification. The bullet-like nanopores showed strong rectification ($R_f$~3.4) only after they were coated with a thin layer ~3 nm of $Al_2O_3$ (FIGS. 8-9). FIG. 9 is a schematic illustration (top) and typical current traces (bottom) of $Al_2O_3$ coated bullet-like polymeric nanopores (10 nm) under applied voltages ranging from −1000 mV to +1000 mV in 1M KCl. These $Al_2O_3$ coated asymmetric polymeric nanopores with bullet-like shape (large cone angles) show strong ionic current rectification behavior, which indicates strong field leakage at the pore tip. In contrast, rectification became much weaker in $Al_2O_3$ coated nanopores with small cone angles (trumpet-like pores) or thick dielectric film (10 nm) due to decreased normal field leakage as expected from Equation (1) (FIG. 7). In the case of bare PET nanopores, the current rectification enhancement was not evident, indicating field leakage is negligible in bare PET nanopores. In addition, the noise characteristics of all $Al_2O_3$-coated PET nanopores showed more than an order of magnitude reduction in higher frequency dielectric noise compared with typical nanopores in dielectric membrane (FIG. 10). Bullet-like nanopores after $Al_2O_3$ coating showed a mild increase in low frequency 1/f noise associated with field leakage induced charge. $Al_2O_3$-coated PET nanopores with bullet shape should hence produce a leakage field within the thin dielectric film to pin translocating molecules with very little interference of the resistive signal.

Field Leakage Effect on the Translocation of DNA

Having fabricated the $Al_2O_3$-coated PET nanopores, the field leakage effect on the translocation of DNA molecules was tested. Twenty-two nt ssDNA molecules (contour length, 6 nm) were selected as a representative small nucleic acid molecules whose fast translocation poses a major challenge to their detection by other solid-state nanopores. FIG. 11 presents typical current traces recorded during the translocation for a bare bullet PET nanopore without $Al_2O_3$ film coating and two bullet nanopores with 3 nm or 10 nm $Al_2O_3$ film coating. Resolvable signals due to translocation events are only observed in bullet nanopores (diameter, 10 nm) coated with 3 or 10 nm $Al_2O_3$ film when substantial field leakage occurs. Moreover, the translocation time strongly depends on the $Al_2O_3$ film thickness. By comparing these two nanopores, an increase of one order of magnitude was seen in the observed average translocation time (from 13 ms to 159 ms) when the thickness of $Al_2O_3$ film decreases from 10 nm to 3 nm (FIGS. 11 and 12). As suggested from the field flux balance, the field leakage at the pore transition area is expected to become stronger with thinner $Al_2O_3$ dielectric layer. In contrast, no translocation event was detected for bare bullet PET nanopores without the high-permittivity dielectric layer that sustains field leakage—it is a singular limit (FIG. 13).

The correlation between dielectric film thickness and translocation time was observed in all tested $Al_2O_3$-coated PET nanopores at different bias voltages. Other than dielectric film thickness, different field leakage strengths can also be fine-tuned by varying cone angles of nanopore or bias voltages as expected from Equation (1). The average translocation time can range from tens of milliseconds to hundreds of seconds (5 orders of magnitude variation) as a function of field leakage strength, as shown in detail below. Previous studies have shown that the translocation of 100 nt ssDNA can be slowed down to ~0.18 ms using solid-state nanopores in $Al_2O_3$ membranes. An average translocation time ~159 ms for 22 nt ssDNA was observed in the $Al_2O_3$-coated PET nanopores with an intermediate field leakage strength. Although a positively charged dielectric $Al_2O_3$ surface can slow down the DNA translocations through electrostatic interactions, such electrostatic interactions with the native surface charge can be ruled out as the dominant interaction for two reasons: (1) the much longer translocation time and (2) the observed film thickness effect on translocation time. It is therefore concluded that the field leakage at the pore transition area is responsible for drastically slowing down the translocation by 5 orders of magnitude.

A simple way to tune the field leakage strength and hence the translocation time is to vary the applied voltage. In other solid-state nanopores, the electrophoretic translocation time of the molecules decreases with increasing applied voltages. In contrast, we found an opposite trend for the 22 nt ssDNA, whose translocation time was found to increase dramatically (exponentially) with increasing applied voltage. FIG. 14 shows sample current traces for typical events under 400 mV and 600 mV along with the translocation time histogram for each corresponding case. When the applied voltage was slightly increased from 400 to 600 mV, the average translocation time increased fivefold from 235 to 1217 ms (FIG. 14). The exponential dependence suggests an activated escape of the pinned molecules from a trapping energy well before they translocate through the nanopore. The high tunability of molecular pinning mechanism by varying the leakage field allows versatile control of translocation process, which is difficult for other interactions (e.g., hydrophobic interactions). It is expected that the molecular persistence length and size can sensitively change the barrier and the translocation time, since the normal leakage field is confined to a film less than 3 nm in width.

This extreme selectivity is confirmed by the 22 nt ssDNA and 22 bp dsDNA translocation experiments. The sample current traces for typical dsDNA translocation events and translocation time histograms at applied voltages of 400 mV and 600 mV are shown in FIG. 15. Interestingly, at both voltages, the translocation speed for dsDNA is observed to be orders of magnitude faster than that for the ssDNA. For example, at 600 mV, the average translocation time of dsDNA is 1.5 ms, which is three orders of magnitude shorter than that of the ssDNA. The translocation time of dsDNA has an opposite voltage-dependence to the ssDNA. Increasing the applied voltages from 400mV to 600 mV, the translocation time of dsDNA decreases from 4 ms to 1.5 ms. These observations suggest that the normal leakage field has much less effect on dsDNA translocation and the energy barrier resulting from the electrostatic trap at the pore edge does not render dsDNA translocation an activated event with a field-dependent barrier. With the opposite trends of ssDNA and dsDNA translocation times on voltage bias, the mean translocation times of the two molecules are about a factor of ~811 different at 600 mV and, taking into account the spread in their distributions, the probability of a ssDNA exhibiting the same translocation time as a dsDNA is less than 3% (FIG. 14 and FIGS. 16-18).

FIG. 16 shows representative current traces for 22 nt ssDNA, 22 bp dsDNA, and the mixture of 22 nt ssDNA and 22 bp dsDNA (1:1) translocation through bullet-shaped nanopores (10 nm, half cone angle ~7±2°) coated with 3 nm $Al_2O_3$ film under an applied voltage of 500 mV. FIG. 17 is a schematic of 22 nt ssDNA and 22 bp dsDNA translocation under the effect of electric field leakage. ssDNA molecules (persistence length, 2 nm) can easily deform and be pinned at the pore edge. The stiffer dsDNA molecule (persistence length, 50 nm) tends to be linearly oriented under the influence of the strong local electric field and could be expected to have weak interactions with the leakage field. FIG. 18 is a normalized histogram of translocation times for 22 nt ssDNA and 22 bp dsDNA. ssDNA translocates much slower than dsDNA under the effect of electric field leakage (for a nanopore with intermediate field leakage, typical translocation time ~1 ms (dsDNA) vs. ~100 ms (ssDNA)). These signature electrical signals allow discrimination (>97%) between ssDNA and dsDNA duplex translocation events. Since an excess of ssDNA molecules with long translocation times will increase the assay time for a given number of translocation events, the selectivity gained at high field comes with a trade-off in longer assay time for ssDNA-rich mixtures (FIG. 19). FIG. 19 illustrates example current recordings for the spiked dsDNA samples mixed with ssDNA with concentrations as indicated. This highly selective sensing does not come with a tradeoff in throughput as long as the ssDNA in the sample is below 10%. When the ssDNA in the sample is above 10%, their long translocation may start to reduce the throughput.

The persistence length for dsDNA molecules is about 50 nm, which is significantly larger than that for ssDNA molecules (2 nm). Other than their drastically different hydrodynamic radii relative to the thickness of the dielectric film, there could also be an orientation effect on the barrier height; ssDNA molecules can easily deform and pin conformally to the edge by the leakage field (FIG. 20). In contrast, the stiffer dsDNA molecule would remain linear and hence experience much weaker electrostatic interaction with the normal leakage field, as schematically shown in FIG. 21. Note that although this normal leakage field induced electrostatic interaction with dsDNA is not as strong as that for ssDNA, the translocation of short dsDNA through the nanopores with the presence of normal field leakage is still slower than that for other solid state nanopores (FIG. 22). FIG. 22 shows example current recordings of 22 bp dsDNA translocation through bullet-shaped PET nanopores (10 nm, half cone angle ~7±2°) coated with 3 nm $Al_2O_3$ film under an applied voltage of 500 mV. Comparison between different solid-state nanopore platforms for short dsDNA translocation. Although this normal leakage field induced electrostatic interaction with dsDNA is not as strong as that for ssDNA, the translocation of short dsDNA through our nanopores with the presence of normal field leakage is still slower than that for other solid-state nanopores.

TABLE 2

| Nanopore | Translocation time (ms) | dsDNA length | Translocation speed |
| --- | --- | --- | --- |
| Graphene-$Al_2O_3$-Graphene | 0.34 | 850 bp dsDNA | 0.4 μs bp$^{-1}$ |
| SiN nanopore | 0.02 | 25 bp dsDNA | 0.8 μs bp$^{-1}$ |
| $Al_2O_3$-PET nanopore | 1 | 22 bp dsDNA | 45 uμ bp$^{-1}$ |

The large difference in ssDNA and dsDNA translocation times offers a sensitive mechanism that can differentiate oligo-hybridized short nucleic acid targets like microRNA (19-22 nt) from the unhybridized non-targets of similar contour lengths.

Delay of Translocation Dynamics by Field Leakage

To realize the full potential of field leakage induced retardation of ssDNA, different geometries were investigated to enhance the field leakage. A series of bullet $Al_2O_3$-coated nanopores (diameter, 10 nm) with different half cone angles at their conical base were used. The nanopores with larger half cone angles allow more electric field to be focused at the nanopore tip under the same applied voltage and thus higher magnitude of normal leakage field at the pore edge. Such asymmetric nanopores with different half cone angles were fabricated by varying etching times after breakthrough (FIG. 23). FIG. 23 graphically illustrates measured half cone angle of the asymmetric PET nanopore as a function of the time of etching under asymmetric conditions after breakthrough. The pore geometry evolves through a variety of configurations (half cone angles) with advancing time after breakthrough. While immediately after breakthrough the pore tips are trumpet-shaped, further etching is strongly affected by osmotic effects which eventually lead to bullet-shaped pore tips. Thus, asymmetric nanopores with different half cone angles can be fabricated by varying etching times after breakthrough.

FIG. 24 compares four representative current traces through four $Al_2O_3$-coated nanopores with half cone angles ranging from 4° to 20°. The magnitude of corresponding electric field $E_0$ at the pore tip is indicated in FIG. 24. Strikingly, with the increase of $E_0$ and thus normal leakage field, the average translocation time can be increased exponentially from tens of milliseconds to hundreds of seconds (FIG. 25). The strong impact of field leakage on ssDNA translocation provides the ability to tune the dynamic range of translocation time up to 5 decades over their dsDNA counterpart by varying the normal leakage field. Compared to dsDNA counterparts, the exponential increase of translocation time of ssDNA with increasing normal field leakage suggests the same leakage field selectively creates a very different barrier for ssDNA.

This difference was further explored by quantifying the translocation time τ and strength of normal leakage field $E_{leak}$. For ssDNA translocation governed by an energy barrier, the translocation time τ is in general described by a Van't Hoff-Arrhenius law:

$$\tau = \tau_0 e^{\frac{E_a}{k_B T}} \quad (2)$$

where $\tau_0$ is the zero field leakage translocation time, $k_B$ is Boltzmann constant, T is the temperature, $E_a = E_{leak} z e l$ is the activation barrier due to the action of the normal leakage field on ze, the effective charge of the ssDNA segment over the region of length l with normal leakage field (FIG. 26). For $Al_2O_3$ film thickness l of 3 nm, the charge ze for the 10 nt segment of ssDNA is about 2.5 e, assuming a Manning screening factor of ~75%. The zero-leakage translocation time $\tau_0$ can be approximated as the typical translocation time (~1 ms) for dsDNA of the same length under weak leakage field (FIGS. 16-18). This approximation is reasonable because the stiffer dsDNA is almost free from the influence of normal leakage field compared with ssDNA. $E_{leak}$ was obtained from Equation (1) and find excellent quantitative fit to the data in FIG. 25 if the relative permittivity of water $\varepsilon_{water}$ reduced from 80 to 6. This adjustment is reasonable, as the dielectric constant of surficial water layer of two to three molecules thick is known to be significantly smaller than that of bulk water (the literature value is 2 to 20) because the rotational freedom of water dipoles decreases for the immobile layers near the surface. Thus, the normal field leakage $E_{leak}$ near the pore transition area becomes higher than normally expected because of the weak screening effect of the immobile water layers. A water permittivity comparable to the dielectric film would indeed produce a leakage field that is comparable to the applied field, according to the thin-film limit of Eq. (1). This may also explain the weaker pinning on dsDNA, whose linear conformation may be outside these few layers of water molecules and experiences a much weaker screened field.

When the energy barrier increases to 12.7 kT ($E_0$=36.4±6.1 V/μm in FIG. 24), the average translocation time of ssDNA can be up to minutes. Even under such strong normal leakage field, this electrostatic trapping effect is completely reversible. This is illustrated in FIGS. 27-28, the current recovered to the base level after a negative applied voltage was applied. FIG. 28 illustrates continuous electrical recording of 22 nt ssDNA pinning at the pore edge under applied voltage of +500 mV (energy barrier, 12.7 kT) and ssDNA escaping from the nanopore after the electrostatic trapping effect is switched off by reversing the polarity of applied voltage to −500 mV. This electrostatic trapping effect is completely reversible.

Once the direction of applied voltage and normal leakage field is reversed, the electrostatic trapping effect is switched off, and ssDNA can escape from the nanopore. This reversible electrostatic trapping effect reduces the possibility of permanent nanopore blocking by translocating molecules, which is a common issue for nanopore sensors. Consistent with this observation, the $Al_2O_3$-coated PET nanopores were found to have a functional lifetime of up to several days without clogging (FIG. 29). FIG. 29 illustrates typical current versus time traces of 22 bp dsDNA translocation events. The reversible and selective electrostatic trapping effect confers non-fouling properties to these pores and enables resistive pulse recordings over several days without clogging. Both recordings are 20 s long; one was taken 0.5 h after addition of the sample and the other, 60 h later.

EXAMPLE 2

Highly Controllable and Reproducible Fabrication of $Al_2O_3$ Coated Polymeric Nanopore for Sensitive miRNA Detection.

Highly controllable fabrication of $Al_2O_3$ coated polymeric nanopore with reproducible shape and size, assists the nanopore-based miRNA quantification with optimal throughput and sensitivity. The systems and methods of the invention represent a new strategy based on electric field leakage to slow down the transport of miRNA as illustrated in FIG. 2A. The degree of electric field leakage across the nanopore tip is controlled by the cone angle. Example 1 demonstrates that the as-prepared nanopores with similar overall cone angles (obtained by using similar etching time after breakthrough) show significant differences in sensing performance in terms of event frequency. Only less than 10% nanopores are capable of high-throughput sensing with reproducible event frequency under the same target concentrations. These performance variations are due to a lack of nanoscale morphology control at the nanopore tip. Even though the as-prepared asymmetric nanopores can have similar overall cone angle, the nanoscale morphology at the nanopore tip can be very different. Only if the asymmetric nanopores with a slender tip (FIG. 30A) the electric field leakage can be focused/enhanced in the thin $Al_2O_3$ film around the nanopore edge. This is evidenced by the comparison of ion current signals before and after the $Al_2O_3$ ALD (Atomic Layer Deposition) coating (FIGS. 30A, 30B, 30C). The enhanced rectification behavior under high ion strength buffer (1 M KCl) due to field leakage effect can be observed only after high-permittivity $Al_2O_3$ film coating rather than in the bare polymer nanopore, indicating the focused and enhanced electric field leakage occurs within the $Al_2O_3$ film. This focused and enhanced electric field leakage around the nanopore edge is critical for sensitive miRNA quantification by slowing down their translocation as evidenced and illustrated in FIG. 31. On the contrary, the asymmetric nanopore with a sharp tip shows enhanced rectification effects for both bare polymer nanopore and $Al_2O_3$ ALD coated nanopore (FIG. 31C), indicating the field also leaks into the polymer nanopore wall and fails to be focused within the $Al_2O_3$ film around the nanopore edge. Thus, the weak normal field fails to slow down the translocation and the weaker tangential field also becomes less efficient to drive the molecular through the nanopore, resulting in low event frequency as shown in FIG. 6. To improve the control of nanoscale morphology at the nanopore tip, the track-etched polymer nanopore etching method was optimized as shown in Table 1. The new etching method achieves greater than 50% success rate to obtain similar nanopores with reproducible high-throughput counting performance. Under the same target concentrations, these nanopores showed consistent translocation frequency, which is essential for quantification in a robust and unbiased manner.

Absolute Quantification of Target miRNA Concentration

Sequence-specific miRNA detection at single-molecule precision with ~1000-1,000,000 copies (fM-pM) dynamic range and high throughput in a 10 μl sample was achieved. As shown in FIG. 32A, single-molecule sensitivity for dsDNA sensing with concentrations ranging from 10 fM to 10 pM or 10,000 to 10 million copies in the 10 μl sample was achieved. From the extrapolated translocation frequency in FIG. 32C, 1000 copies at 1 fM concentration would have a translocation frequency of 1 target translocation event per 60 s or 1 minute. It would take hours to get a statistically significant number of events. It was hence decided not to pursue this lower limit. Typical miRNA concentrations in blood plasma samples reported in the literature and measured in our lab exceed 10 fM in concentration. The current dynamic range was deemed adequate for liquid biopsy applications.

The target dsDNA concentration of a sample can be measured from the frequency of translocation signals as shown in FIG. 32C. It was found that frequency of translocation events are directly proportional to the dsDNA concentration, suggesting that transport of DNA from the solution to the nanopore was the rate limiting step. The field leakage through the $Al_2O_3$ layer also allows long-range trapping such that the translocation frequency for dsDNA at pM is as high as 80 $s^{-1}$ $pM^{-1}$, more than 1,000 times higher than any other solid state nanopore and $10^4$ times higher than protein nanopores. This high translocation frequency enables us to obtain a precise event frequency measurement within ~15 min. FIG. 32D shows 15 min rapid measurement is enough to represent the average translocation frequency for longer duration measurement. ssDNA translocates much slower than dsDNA through an $Al_2O_3$ nanopore (for a nanopore with intermediate cone angle, average translocation time ~100 ms vs. ~1 ms as shown in FIG. 32B), which can be attributed to their conformation differences/different persistence lengths and preferential ssDNA reversible adsorption on the high-permittivity alumina layer by Van der Waals forces at the tips of the nanopores. These signature electrical signals allow discrimination (95%) between ssDNA and dsDNA duplex translocation events, which provide the basis for specific detection of target miRNA. As seen in FIG. 32B, this highly selective sensing does not come with a tradeoff in throughput as long as the ssDNA in the sample is below 10%. When the ssDNA in the sample is above 10%, their long translocation will start to reduce the throughput, we use the necessary integrated chip pretreatment technologies as shown in activity 3 that can achieve such separation so that all target miRNAs in a 10 μl sample can be counted in an unbiased way.

What is claimed is:

1. A system for detecting and quantifying a target single stranded polynucleotide, the system comprising:
   a membrane including an insulative material and a plurality of bullet-shaped nanopores extending between a lower surface and an upper surface of the membrane, each of the bullet-shaped nanopores including a first opening and a second opening thereby defining a passageway through the membrane;
   a thin high-permittivity dielectric material coating the passageway and at least a portion of the upper surface;
   wherein the passageway defines a first longitudinal axis and includes a first inner diameter at the first opening and a second inner diameter at the second opening, wherein the first diameter is smaller than the second diameter,
   wherein the passageway diverges from the first opening to a first section of the passageway at a first slope and wherein the passageway diverges from the first section to the second opening at a second slope,
   wherein the first opening intersects the upper surface at the first inner diameter,
   wherein a second longitudinal axis, parallel to the longitudinal axis, intersects the first inner diameter and defines an angle with an adjacent inner surface of the passageway,
   wherein application of an electric field to the membrane traps the single stranded polynucleotide due to an electric leakage field through the thin high-permittivity dielectric material at the first opening.

2. The system of claim 1, wherein the insulative material is a polymer.

3. The system of claim 2, wherein the polymer is polyethylene terephthalate.

4. The system of claim 1, wherein the thin high-permittivity dielectric material is $Al_2O_3$.

5. The system of claim 1, wherein the thin high-permittivity dielectric material covers the upper surface and the lower surface.

6. The system of claim 1, wherein the first inner diameter is in a range of 4 nm to 50 nm.

7. The system of claim 1, wherein the first inner diameter is in a range of 5 nm to 20 nm.

8. The system of claim 1, wherein the first inner diameter is 8 nm.

9. The system of claim 1, wherein the thin high-permittivity dielectric material includes a thickness in a range of 1 nm to 10 nm.

10. The system of claim 1, wherein the thin high-permittivity dielectric material includes a thickness in a range of 2 nm to 5 nm.

11. The system of claim 1, wherein the thin high-permittivity dielectric material includes a thickness of 3 nm.

12. The system of claim 1, wherein the angle is between 4 degrees and 20 degrees.

13. The system of claim 1, wherein the angle is between 5 degrees and 10 degrees.

14. The system of claim 1, wherein the first slope is between 2 degrees and 30 degrees.

15. The system of claim 1, wherein the second slope is between 1 degrees and 20 degrees.

16. The system of claim 1, wherein the intersection between the first opening and the upper surface defines an edge contoured substantially in the form of a curve.

17. The system of claim 16, wherein a tangent, parallel to the longitudinal axis, at the first inner diameter defines an angle with an adjacent inner surface of the passageway.

18. The system of claim 1, wherein the single stranded polynucleotide remains trapped at the first opening based on a persistence length of the single stranded polynucleotide.

19. The system of claim 1, wherein the single stranded polynucleotide is trapped or not trapped at the first opening based on a molecular tag of the single stranded polynucleotide or based on the single stranded polynucleotide forming a complex.

20. A method of delaying translocation of a target single stranded polynucleotide, the method comprising:
   applying an electric field to a membrane having a nanopore edge to enhance a leakage field, the membrane including
      a plurality of bullet-shaped nanopores extending between a lower surface and an upper surface of the membrane, each of the bullet-shaped nanopores including a first opening and a second opening thereby defining a passageway through the membrane;
      a thin high-permittivity dielectric material coating the passageway and at least a portion of the upper surface;
      the passageway defining a first longitudinal axis and including a first inner diameter at the first opening and a second inner diameter at the second opening, wherein the first inner diameter is smaller than the second inner diameter,
      wherein the passageway diverges from the first opening to a first section of the passageway at a first slope and wherein the passageway diverges from the first section to the second opening at a second slope,
      wherein the first opening intersects the upper surface at the first inner diameter,
      wherein a second longitudinal axis, parallel to the first longitudinal axis, intersects the first inner diameter and defines an angle with an adjacent inner surface of the passageway,
   temporarily trapping the target single stranded polynucleotide at the first opening.

21. The method of claim 20, further comprising applying a negative electric field to release the single stranded polynucleotide from the first opening.

* * * * *

UNITED STATES PATENT AND TRADEMARK OFFICE
CERTIFICATE OF CORRECTION

Page 1 of 1

PATENT NO.         : 11,162,935 B2
APPLICATION NO.    : 16/550766
DATED              : November 2, 2021
INVENTOR(S)        : Ceming Wang, Satyajyoti Senapati and Hsueh-Chia Chang It is certified that error appears in the above-identified patent and that said Letters Patent is hereby corrected as shown below:

In the Specification

Column 1, Line 14, please insert the following paragraph:
-- STATEMENT OF GOVERNMENT INTEREST
This invention was made with government support under Grant No. CA206904 awarded by the National Institutes of Health. The government has certain rights in the invention. --

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*